United States Patent

Donadio, III

[11] Patent Number: 6,027,863
[45] Date of Patent: *Feb. 22, 2000

[54] METHOD FOR MANUFACTURING A TUBULAR MEDICAL DEVICE

[75] Inventor: James V. Donadio, III, Chaska, Minn.

[73] Assignee: Intratherapeutics, Inc., St. Paul, Minn.

[*] Notice: This patent issued on a continued prosecution application filed under 37 CFR 1.53(d), and is subject to the twenty year patent term provisions of 35 U.S.C. 154(a)(2).

[21] Appl. No.: 08/645,607

[22] Filed: May 14, 1996

Related U.S. Application Data

[63] Continuation-in-part of application No. 08/455,331, May 31, 1995, Pat. No. 5,741,429, and application No. 08/329,691, Oct. 26, 1994, Pat. No. 5,573,520, which is a continuation of application No. 07/940,657, Sep. 4, 1992, abandoned, which is a continuation-in-part of application No. 07/755,614, Sep. 5, 1991, abandoned.

[51] Int. Cl.[7] ............................................. G03F 7/26
[52] U.S. Cl. ........................... 430/320; 430/394; 430/396; 430/397; 216/9
[58] Field of Search .................................. 430/311, 312, 430/313, 318, 320, 323, 394, 396, 397; 156/643.1, 659.11; 216/8, 9, 10, 45, 49

[56] References Cited

U.S. PATENT DOCUMENTS

| | | |
|---|---|---|
| 3,071,942 | 1/1963 | Alcaro . |
| 3,390,546 | 7/1968 | Jewell . |
| 3,668,030 | 6/1972 | Broderick . |
| 3,844,137 | 10/1974 | Zugel . |
| 3,883,353 | 5/1975 | Cohen et al. . |
| 4,037,075 | 7/1977 | Pugsley et al. . |
| 4,059,479 | 11/1977 | Tanazawa . |
| 4,102,734 | 7/1978 | Schiffman . |
| 4,108,683 | 8/1978 | Anderson . |
| 4,262,186 | 4/1981 | Provancher . |
| 4,432,853 | 2/1984 | Banks et al. . |
| 4,465,482 | 8/1984 | Tittel . |
| 4,504,354 | 3/1985 | George et al. . |
| 4,580,551 | 4/1986 | Siegmund et al. . |
| 4,716,270 | 12/1987 | Gnanamuthu et al. . |
| 4,733,665 | 3/1988 | Palmaz . |
| 4,739,762 | 4/1988 | Palmaz . |
| 4,767,418 | 8/1988 | Deininger et al. ........................ 623/1 |
| 4,776,337 | 10/1988 | Palmaz . |
| 4,893,623 | 1/1990 | Rosenbluth . |
| 4,911,148 | 3/1990 | Sosnowski et al. . |
| 4,959,275 | 9/1990 | Iguchi et al. . |
| 4,998,923 | 3/1991 | Samson et al. . |

(List continued on next page.)

FOREIGN PATENT DOCUMENTS

| | | |
|---|---|---|
| 0 047 231 A2 | 3/1982 | European Pat. Off. . |
| 0 062 300 | 3/1982 | European Pat. Off. . |
| 0 256 938 | 2/1988 | European Pat. Off. . |
| 0 338 816 A2 | 4/1989 | European Pat. Off. . |
| 0 361 192 | 9/1989 | European Pat. Off. . |
| 0 364 787 A1 | 9/1989 | European Pat. Off. . |
| 0 407 951 A2 | 7/1990 | European Pat. Off. . |
| 0 608 853 A2 | 1/1994 | European Pat. Off. . |
| 0608853 | 8/1994 | European Pat. Off. . |
| 0 709 067 A2 | 5/1996 | European Pat. Off. . |
| 5-225641 | 9/1993 | Japan . |
| WO 91/07139 | 10/1990 | WIPO . |
| WO 93/04722 | 3/1993 | WIPO . |
| 96/38193 | 12/1996 | WIPO . |

*Primary Examiner*—Kathleen Duda
*Attorney, Agent, or Firm*—Merchant & Gould P.C.

[57] ABSTRACT

Manufacturing processes for apparatus, including slotted hypotube, for use as a catheter, a guidewire, a catheter sheath for use with catheter introducers or a drug infusion catheter/guidewire are disclosed. The manufacturing process includes creating a pattern of slots or apertures in a flexible metallic tubular member, by processes including but not limited to, electrostatic discharge machining (EDM), chemical milling, ablation and laser cutting. These slots or apertures may be cut completely or partially through the wall of the flexible metallic tubular member. These manufacturing processes may include the additional step of encasing the flexible metallic member such that a fluid tight seal is formed around the periphery of the tubular member.

29 Claims, 17 Drawing Sheets

U.S. PATENT DOCUMENTS

| | | |
|---|---|---|
| 5,047,116 | 9/1991 | Luthie et al. . |
| 5,073,694 | 12/1991 | Tessier et al. . |
| 5,095,915 | 3/1992 | Engleson . |
| 5,102,417 | 4/1992 | Palmaz . |
| 5,147,763 | 9/1992 | Kamitakahara ......................... 430/320 |
| 5,195,984 | 3/1993 | Schatz . |
| 5,228,441 | 7/1993 | Lundquist . |
| 5,269,882 | 12/1993 | Jacobsen . |
| 5,315,996 | 5/1994 | Lundquist . |
| 5,322,064 | 6/1994 | Lundquist . |
| 5,348,616 | 9/1994 | Hartman et al. . |
| 5,421,955 | 6/1995 | Lau et al. . |
| 5,481,184 | 1/1996 | Jacobsen . |
| 5,514,154 | 5/1996 | Lau et al. . |
| 5,741,429 | 4/1998 | Donadio, III et al. ..................... 216/8 |

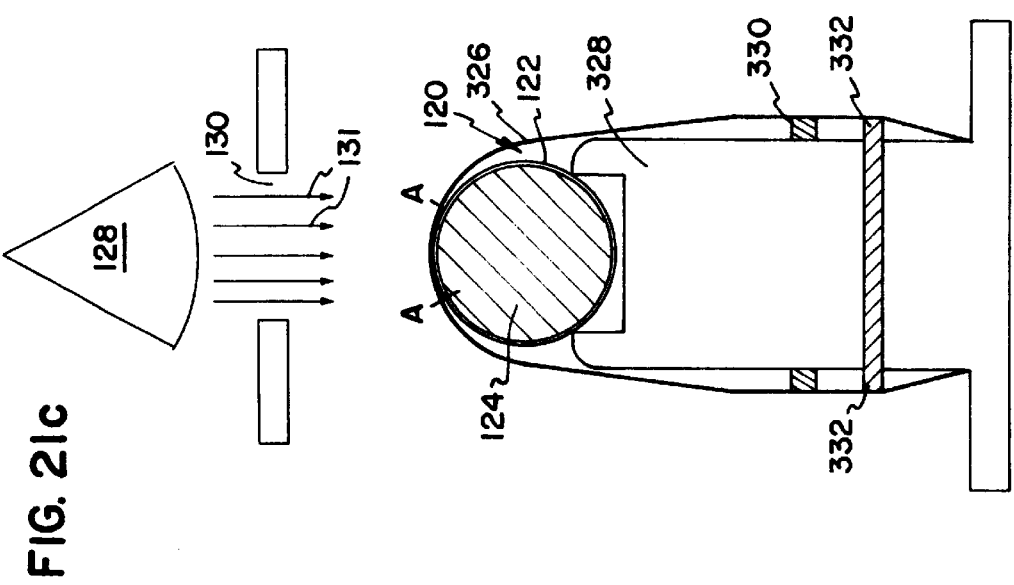

METHOD FOR MANUFACTURING A TUBULAR MEDICAL DEVICE

The following is a continuation-in-part of application Ser. No. 08/455,331, filed May 31, 1995, which issued as U.S. Pat. No. 5,741,429 and is a continuation-in-part of application Ser. No. 08/329,691 filed Oct. 26, 1994 now U.S. Pat. No. 5,573,520, which is a continuation of application Ser. No. 07/940,657 filed Sep. 4, 1992, now abandoned, which is a continuation-in-part of application Ser. No. 07/755,614 filed Sep. 5, 1991, now abandoned.

BACKGROUND OF THE INVENTION

The present invention relates to a biocompatible flexible tubular device for insertion into the body during medical procedures. More particularly, the invention relates to flexible tubular devices for use as catheters, including guide catheters and balloon catheters, guidewires, catheter sheaths, catheter introducers, drug infusion catheters/guidewires, and methods for making the same.

Catheters and Guidewires

Catheters are relatively thin and flexible tubes used in the medical field for numerous applications. Catheters are made by any number of different methods and designs. However, in most catheter designs it is desirable to obtain a maximum torsional rigidity while retaining a satisfactory longitudinal flexibility and stiffness without kinking. These features will allow the orientation of the catheter to be manipulated so that the catheter can be guided through small body vessels and cavities. These features will also prevent any kinking from occurring, and provide the catheter with enough "push" or stiffness so as to prevent the catheter from wrinkling or folding back on itself during this process. The specific nature of these characteristics will of course vary depending on the specific application for which the catheter is being used. Yet another consideration is that a relatively small outside diameter must be maintained while providing a lumen or an inside diameter as large as possible.

Guide wires require the same general type of characteristics. However, with guide wires it is important to minimize the outside diameter of the guide wire so that they will readily fit inside of the lumen of the catheter.

Catheters and guide wires are used both as diagnostic tools and in the treatment of diseases. One such diagnostic procedure is cardiac catheterization which is a widely performed procedure, being used for assessment of coronary artery disease. Other uses are neurologic uses, radiologic uses, electrophysiologic uses, peripheral vascular uses, etc. One example of a treatment use is the use of balloon catheters in dilation procedures to treat coronary disease. Dilation procedures rely upon the use of a catheter for injection of contrast and delivery of guidewires and dilation catheters to the coronary artery or other arteries. An example of the use of guide wires is for Percutaneous Transluminal Coronary Angioplasty (PTCA) balloons and for guiding diagnostic catheters through the arteries and to body organs.

The catheters and guide wires used in these and other procedures must have excellent torque characteristics, and must have the requisite flexibility. In addition, it is important that catheters and guidewires provide sufficient longitudinal support for "pushing" of items through the arteries and other vessels such as when feeding the balloon portion of an angioplasty catheter through the arteries. Unless there is sufficient stiffness, the catheter or guidewire will wrinkle or fold back on itself.

Typically, in the case of a catheter, the larger the ratio of inside to outside diameter, the better. For guide wires it is important to maintain a small outside diameter. Smaller catheter and guidewire outside diameter sizes result in less chance of arterial damage.

Catheters and guide wires must have sufficient torque such that they do not buckle when being manipulated. Finally, flexibility is important so that the catheter or guide wire can be manipulated into the varying arterial branches encountered by the catheter. The guide wire must resist being inadvertently kinked as this results in loss of torque control.

Prior art catheters are typically made of flexible materials which are reinforced such that the resulting composite catheter approximates the desired characteristics. In alternative approaches, guide wires are used in conjunction with catheters to assist in manipulating and moving the catheters through the arterial system in the body.

U.S. Pat. No. 4,020,829 to Willson et al. discloses a spring guide wire for use in catheterization of blood vessels. The guide wire is axially slidable within a thin walled, flexible plastic catheter. The distal portion of the guide wire is of a relatively short length and is connected to a relatively long, manipulative section capable of transmitting rotational torque along its length. In this invention the catheter tube might be advanced over the guide wire after the guide wire has been properly positioned or the catheter might be advanced together with the guide wire, the guide wire providing a reinforcement for the thin wall of the catheter.

U.S. Pat. No. 4,764,324 to Burnham discloses a method for making a catheter. In Burnham, a reinforcing member is heated and applied to a thermoplastic catheter body so as to become embedded in the wall of the catheter. The wall of the catheter is then smoothed and sized so as to produce a composite, reinforced catheter.

The art of applying braiding or multi-pass wire reinforcement to a catheter inner core is also well developed and machinery for performing such a step is well known. Typically, such reinforcement material is applied to the inner core tube of the catheter in a pattern of overlapping right and left hand helices. The braiding process usually requires that the machinery performing the braiding process to move the reinforcement material alternately radially inwardly and outwardly, as well as circularly, whereby the tension of the reinforcement material continuously varies. This varying tension can result in the reinforcement material breaking particularly as the speed of braiding increases. Yet another problem with braided catheters is that their inside diameter is relatively small compared to their outside diameter. The braids are quite loose also.

Current catheters often suffer from either problems of torque, size, flexibility, kinking, and poor support during PTCA in the case of guide catheters. Moreover, catheters cannot be readily made with variable stiffness along the length of the catheter.

Catheter Sheaths and Introducers

Catheter sheaths and introducers are used to provide a conduit for introducing catheters, fluids or other medical devices into blood vessels. A catheter introducer typically comprises a tubular catheter sheath, a hub attached to the proximal end of the sheath having hemostasis valve means to control bleeding and to prevent air embolisms, and a removable hollow dilator that is inserted through the hub, valve means and the lumen of the catheter sheath. Many catheter introducers also contain a feed tube that is connected to the hub to facilitate the introduction of fluids into the blood vessel.

The procedure for positioning the introducer into a blood vessel begins by inserting a hollow needle through the skin and into the lumen of the desired blood vessel. A guidewire is then passed through the needle and into the blood vessel. The needle is then removed leaving the guidewire in the vessel. Next, the sheath and dilator are advanced together over the guidewire until the distal ends of the dilator and sheath are positioned within the lumen of the vessel. The guidewire and dilator are then removed, leaving the distal end of the sheath within the vessel. Catheters or other medical devices can then be passed through the introducer and sheath into the desired vessel.

Conventional sheaths are made of plastic and as shown in FIG. 14, are subject to kinking if bent without internal support. This kinking can occur during the insertion of the device or if the patient moves while the sheath is in the vessel. Unfortunately, this kinking can create sharp edges or irregularities in the sheath that can damage blood vessel linings. This kinking can also make the introduction of devices or fluids more difficult and can cause patient bleeding problems around the sheath tubing. Therefore, there arises a need for a catheter introducer with a catheter sheath that is flexible and resistant to kinking.

Conventional catheter sheaths also have a limited hoop strength making them susceptible to burring or notching. This burring and notching can occur during the insertion of the sheath and dilator into the blood vessel or if the forces exerted on the sheath cause it to become non-circular. These burrs and notches can also damage blood vessel linings. Therefore, there arises the need for a catheter sheath that has sufficient hoop strength to prevent deformation in the sheath to resist the formation of burrs or notches.

It is also important that the sheath have a minimum thickness to reduce the size of the puncture hole in the blood vessel. Larger puncture holes make hemostasis more difficult upon removal of the sheath. The sheath should also be lubricous to make the insertion and extraction of the sheath and other devices easy. Therefore, there arises the need for a catheter sheath for use with a catheter introducer that has a thin wall, that is flexible and resistant to kinking, that is lubricous, and that has sufficient hoop strength to prevent the catheter sheath from burring or notching.

One method for creating a sheath that may meet the above requirements would be to make the sheath from expanded polytetrafluoroethylene (PTFE) as disclosed in U.S. Pat. No. 5,066,285. While PTFE is more flexible and has a higher hoop strength than the plastics used in conventional sheaths, it is still a plastic-type material that may be subject to the same deformation problems.

Drug Infusion Catheters/Guidewires

Drug infusion catheters/guidewires are devices that act like both catheters and guidewires and are capable of delivering drugs or other fluids to a specific location within a patient's blood vessel such as an occluded blood vessel. The guidewire type devices are typically comprised of a coil spring with a heat shrunk TEFLON® coating and a core wire that can be inserted and removed from the lumen in the coil spring. The coated coil also contains either side holes or an end hole or a combination thereof in its distal end to enable the drugs or other fluids to be sprayed into the blood vessel.

During use, the coated coil spring and its core wire are advanced together through the patient's circulatory system much like conventional guidewires. Upon reaching the desired location, the core wire is removed creating a small catheter like device. Drugs or other fluids are pumped through the lumen in the coated coiled spring, out of the holes and into the blood vessel at the desired location.

Because these devices act like guidewires, the outside diameter of the devices, and therefore the lumen, are limited in size. Therefore, a second type of drug infusion catheter/guidewire device utilizes a catheter like member with side holes and a tapered distal end having an end hole generally equal to the outside diameter of a guidewire. These catheter type drug infusion catheter/guidewire devices are advanced over a guidewire to the desired location and then drugs are then pumped through and out of the holes in the catheter like member. These devices can also be used in combination with the guidewire type drug infusion devices.

As described above, drug infusion catheter/guidewire devices act like both catheters and guidewires. Therefore, these devices must have the same characteristics as catheters and guidewires. These devices must obtain a maximum torsional rigidity while retaining a satisfactory longitudinal flexibility and stiffness without kinking. They must also maintain a small outside diameter while providing a lumen as large as possible.

SUMMARY OF THE INVENTION

The present invention relates to a novel apertured flexible tubular member with an encasing for insertion into vessels of the body as part of a medical device. For example, the invention can be used as catheters, including guide catheters and balloon catheters, guidewires, catheter sheaths for use with catheter introducers, or drug infusion catheter/guidewires.

The preferred embodiment of the present invention will be coated with a low friction material such as a low friction polymer so as to provide for lubricity. Samples of materials that might be used are polyurethane, hydrogels, polyethylene, polytetrafluoroethylene (PTFE) and, in particular, one such material which might be used is TEFLON®.

In some embodiments, such as catheters or sheaths, the inside of the flexible tubular member is also preferably coated with a low friction material such as hydrogel and/or with an anticoagulant such as heparin. The coating process might be accomplished by any number of well known processes.

In yet another embodiment of the invention, slots of a predetermined configuration are cut into a single, hollow, thin walled metal tube at predetermined spacings, depth and pattern so as to provide the tube with a desired flexibility. The tube is then encased in a suitable low friction material as noted above or some other suitable coating material.

The use of the flexible tubular member within a fluid-tight encasing provides flexibility to catheters, guidewires, catheter sheaths and drug infusion catheter/guidewires without subjecting them to the possibility of kinking. In addition, because a metal tube is used, these devices also have high hoop strength, therefore, they are resistant to the forming of burrs or notches. Catheter sheaths made from the present invention can also be adapted for use with any conventional catheter introducer parts to create an improved catheter introducer device.

The present invention is further explained hereafter with more particularity and reference to the preferred embodiment shown in the following drawings.

DETAILED DESCRIPTION OF THE DRAWINGS

In the drawings wherein like reference numerals indicate corresponding parts throughout the several views:

FIGS. 21a, 21b and 21c are side views of a manufacturing method for creating slots in a thin-walled tube as shown in FIG. 17;

DETAILED DESCRIPTION OF THE PREFERRED EMBODIMENT

Figure 1:
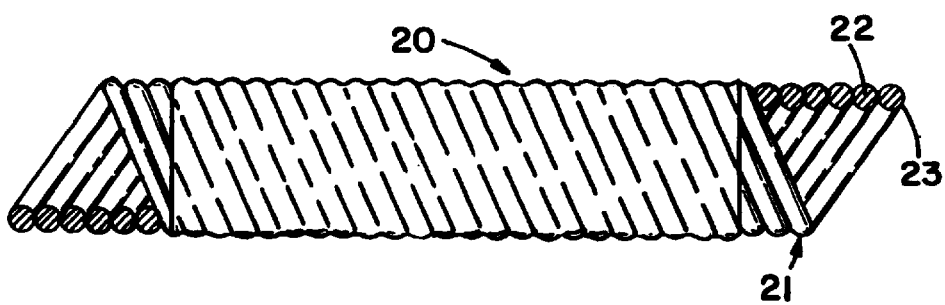
FIG. 1 is a partial view of an embodiment of a catheter, guidewire, catheter sheath or drug infusion catheter/guidewire in accordance with the principles of the invention wherein individual wound filaments comprise substantially round wire.
Figure 2:
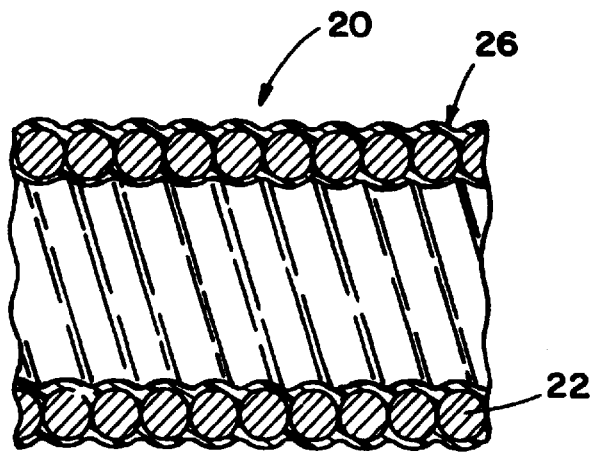
FIG. 2 is a sectional view of the embodiment shown in FIG. 1.
Figure 3:
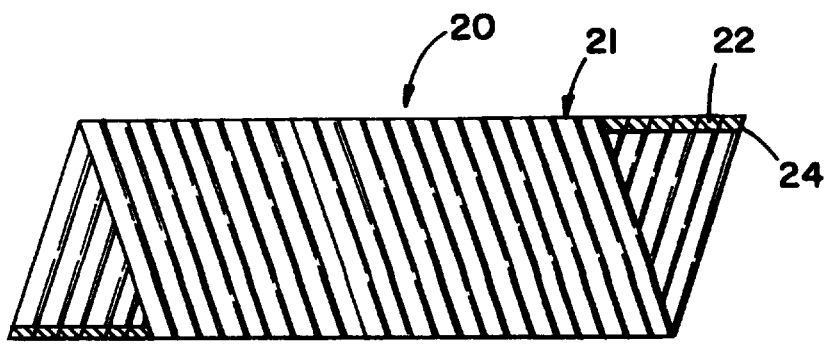
FIG. 3 is a partial view of an alternative embodiment of the present invention wherein the filaments comprise substantially flat ribbon.

Referring now to the drawings, FIGS. 1–3 illustrate two embodiments of a coated flexible tubular member in accordance with the principles of the present invention, generally referred to by the reference numeral 20, for use as a catheter, guidewire, catheter sheath or drug infusion catheter/guidewire. As illustrated in FIGS. 1 and 2, the flexible tubular member 20 has a single layer multiwire coil 21 including six wire filaments 22 which in this case comprise substantially round wire. It will be appreciated that differing numbers of filaments might be used; e.g. two to sixteen or more. In one embodiment, the filaments 22 are made of spring tempered, stainless steel. In another embodiment, the filaments are made of nitinol or ELGILOY®, which is a cobalt-nickel-chromium alloy. The diameter of the wire, in the embodiment shown, is preferably 0.002 inches to 0.010 inches. It will also be appreciated that a single filament coil or multi-layer coil could be used with the invention.

As illustrated, both of the embodiments shown in FIGS. 1–3 are preferably encased in a low friction material such as a low friction polymer or hydrogel for lubricity and to decrease thrombogenicity. Examples of materials which might be used are polyurethane, polyethylene, PTFE or TEFLON®. The thickness of this coating is typically 0.010 inches or less. Preferably the thickness of the coating will be less than the thickness of the filaments. The coating could be applied in one of any well-known methods, such as dip coating, heat shrinking, spray depositing or vapor depositing the material to the coil 21.

Illustrated in FIG. 3 is a helically wound single layer multiwire coil 21 wherein the filaments 22 are made of flat ribbon 24. It will be appreciated that by varying the configuration of the multi-wire coil, a coated flexible tubular member 20 of varying characteristics can be formed. For example, making the individual coils more circular will result in a flexible tubular member 20 which has a greater hoop strength and stiffness, while making the individual coils more longitudinally extending will result in less hoop strength but more flexibility. Having fewer filaments, will result in increased flexibility but less hoop strength. Increasing the size of the filaments will result in increased hoop strength but less flexibility.

Moreover, varying the configuration of the multi-wire coil along the length of the flexible tubular member 20 can result in a flexible tubular member 20 with varying characteristics.

For example, the middle section of the flexible tubular member 20 could be made more flexible by reducing the diameter, reducing the number of filaments, increasing the spacing between filament coils, etc., while the distal end of a flexible tubular member 20 could be arranged to have a higher hoop strength to prevent burring or notching. A flexible tubular member 20 could also be made where the distal end is very flexible and the proximal end is very stiff to improve the transmission of a torque at the proximal end to the distal end. Moreover, a flexible tubular member 20 can be made which varies in stiffness continuously throughout its length. A flexible tubular member 20 can also be made wherein the variation in flexibility or stiffness from one location to the next is very gradual and continuous.

In addition, the flexibility of the flexible tubular member 20 could also be reduced by selectively welding adjacent windings of the coil 21. By welding adjacent windings, the relative movement between the windings is eliminated and the flexibility of the coil in the area adjacent to the weld would be reduced. Therefore, a flexible tubular member 20 having variable flexibility along its length could be made from a coil 21 with a single winding configuration that had selective windings welded together.

Figure 5:
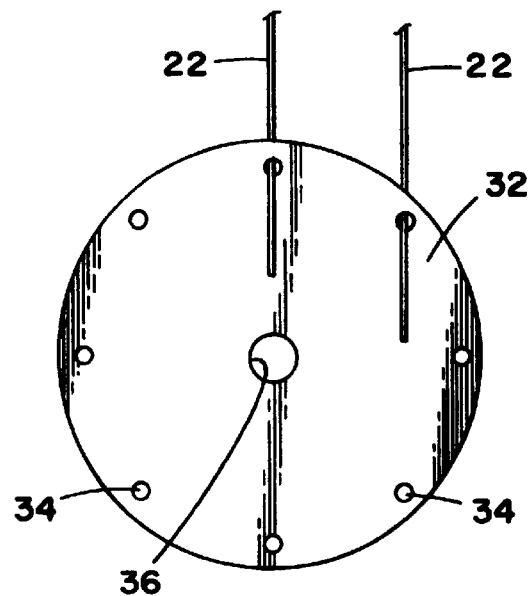
FIG. 5 is an elevational view of an embodiment of a multifilament jig which might be used in accordance with the principles of the present invention.
Figure 4:
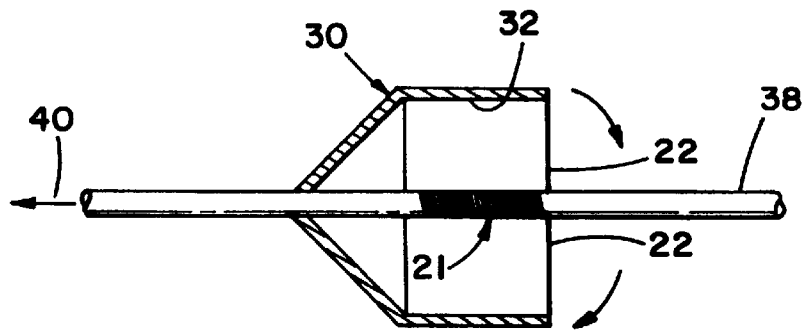
FIG. 4 is an elevational schematic illustration showing a multiple filament jig winding filaments onto a mandrel in accordance with the principles of the present invention.

Illustrated in FIGS. 4 and 5 is one method for making the flexible tubular member 20 embodiment shown in FIGS. 1–3. As shown in FIG. 4, a jig 30 has a portion 32 with apertures 34 disposed therein generally about its periphery. The filaments 22 are slidably disposed in the apertures 34 and are fed from supply reels or the like (not shown). The center of the jig 30 has an aperture 36 for insertion therethrough of a mandrel 38. The mandrel 38 would typically have a diameter of one inch or less. The ends of the filaments 22 are suitably attached to the mandrel 38 at the beginning of the winding process. It will be appreciated that the jig 30 might take on any number of suitable configurations. For example, as opposed to apertures, guide arms might be used to guide the filaments. Moreover, the jig might be replaced with a plurality of arms which are movable radially toward and away from the mandrel.

As illustrated in FIG. 4, the mandrel 38 is inserted through the aperture 36 in the jig 30 and the mandrel 38 is rotated as the mandrel 38 is moved in a downstream direction as generally indicated by the arrow 40. As a result, the filaments 22 are wound onto the mandrel so as to form the single layer multiwire coil 21. The filaments 22 are maintained under very high tension as they are wound onto the mandrel. The tension of course will vary depending on a number of factors. Varying the rate of rotation and the rate of longitudinal movement will result in varying configurations of coils.

The coil 21 is then encased in a suitable low friction material as noted above so as to form a coated flexible tubular member 20 for use as a catheter, guidewire, catheter sheath or drug infusion catheter/guidewire. In one embodiment, the mandrel is moved longitudinally and is rotated, although the jig could just as well be moved and rotated. A typical speed of movement might be one inch per minute, while a typical rate of rotation might be ten revolutions per minute (RPM).

A programmable controller might be used to control the operation of the jig 30 and the mandrel 38 so as to enable precise control of the winding process such that very specific coil configurations can be achieved as well as variations thereof. Those skilled in the art would recognize that several other well known coil winding methods could be used with the invention.

Illustrated in FIGS. 6–10 are alternative embodiments of the flexible tubular member 20 for use as a catheter, guidewire, catheter sheath or drug infusion catheter/guidewire. These embodiments comprise a single metal tube 50, with a wall thickness of roughly 0.001 inches to 0.010 inches. The tube 50 has a plurality of slots 52 disposed therein to form a flexible tubular member 20. The preferred tube material would be stainless steel or nitinol, however, the tube material could be spring temper steel such as the product brand ELGILOY®, or another suitable alloy material. The tube 50 is encased in a suitable low friction material as noted above for the embodiments shown in FIGS. 1–3 so as to seal off the slots making it fluid tight. The inner surface of the tube 50 is preferably coated with a similar low friction material such as TEFLON®, PTFE or FEP so as to provide low friction. Typically the thickness of the outer and inner coating will be 0.001 inches to 0.003 inches or less. It will be appreciated that by varying the configuration of the slots, their depth, and the spacing between the slots, the flexibility, longitudinal stiffness and hoop strength of the flexible tubular member 20 can be varied. In addition, the variation of the composition and thickness of the coating material will also vary the flexibility of the coated flexible tubular member 20 for use as a catheter, guidewire, catheter sheath or drug infusion catheter/guidewire. Moreover, the metal tube 50 might be bent and heat treated to pre-form curves and configurations as desired.

In one embodiment, the slots are cut totally through the tubing wall 50 by use of a an electrostatic discharge machining tool (EDM). To cut the slots using the EDM machine, both ends of the tube 50 are fastened to a holding device such that the tube 50 is positioned between two or more EDM wires. The holding device would then position the tube 50 at the desired location for cutting a slot. The EDM wires would then be moved inward to cut the desired slot. The EDM wires would then translate outward beyond the outer diameter of the tube 50. The holding device would then rotate and/or translate the tube 50 to the desired position for cutting another set of slots. The EDM wires would then be moved inward to cut the next set of slots. This procedure would be repeated throughout the tube 50 to create a flexible tubular member 20. Those skilled in the art would recognize that multiple holding devices and multiple EDM wires could be used to simultaneously cut multiple slots into multiple tubes 50 to simultaneously create multiple flexible tubular members 20.

Figure 17:
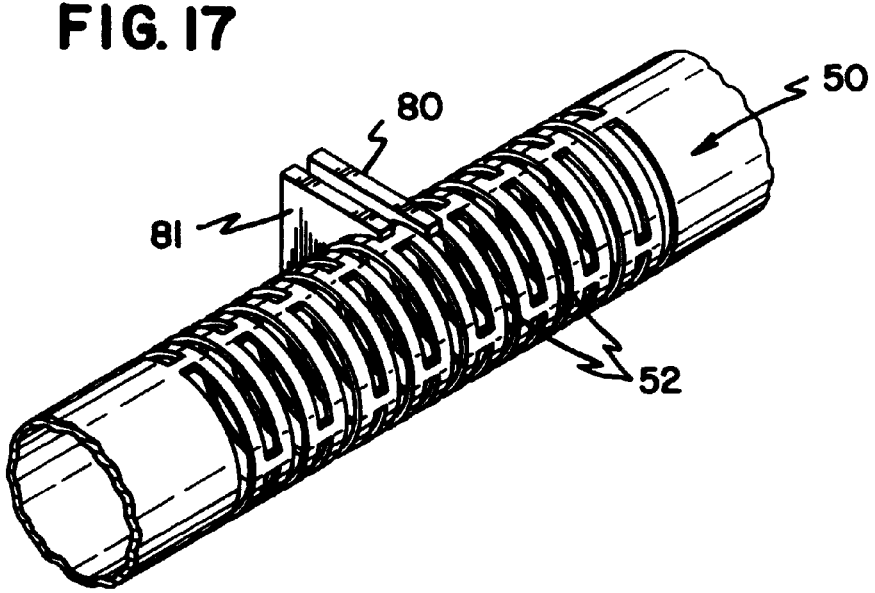
FIG. 17 is a partial perspective view of an alternate embodiment of a catheter, guidewire, catheter sheath or drug infusion catheter/guidewire made in accordance with the principals of the present invention wherein slots are cut into a wall of a thin-walled tube by electrodes from an electrostatic discharge machining tool.

In the preferred embodiment, the slots are cut totally through the tubing wall 50 by use of a plunge EDM machine. As recognized by those skilled in the art, a plunge EDM machine utilizes charged electrodes that are arranged and configured to cut a predetermined shape when they are plunged into a base material. As shown in FIG. 17, a plunge EDM machine with first and second electrodes 80, 81 can be utilized to cut an alternating pattern of slots 52 in the thin-walled tube 50 that are offset by 90°.

Figure 18:
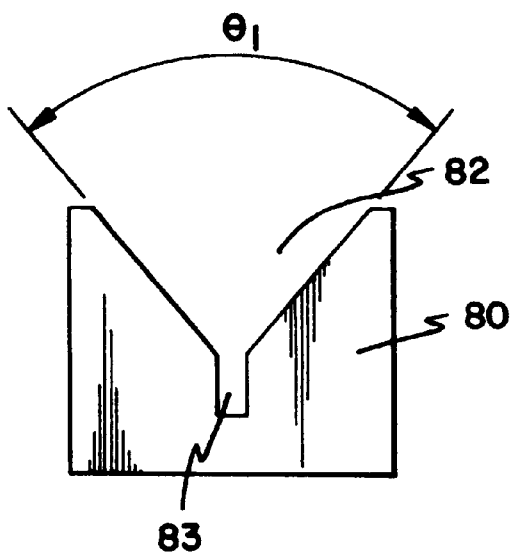
FIG. 18 is a side elevational view of a first electrode for cutting slots in a thin-walled tube as shown in FIG. 17.

As shown in FIG. 18, the first electrode 80 would be generally rectangular in shape with a notch 82 that is triangular in shape with a rectangular extension 83. The depth of the notch 82 would be greater than the radius of tube 50 such that a portion of the tube 50 would be displaced within the rectangular extension 83 of the notch 82 when the first electrode 80 is plunged into the tube 50. Because a portion of the tube 50 is displaced within the rectangular extension 83, that portion is not in contact with the first electrode 80 and is not cut. One example of a first electrode 80 for cutting slots 52 as shown in FIG. 17 would have an angle $\theta_1$ of 82° and a rectangular extension 83 with a width of 0.010 inches.

Figure 19:
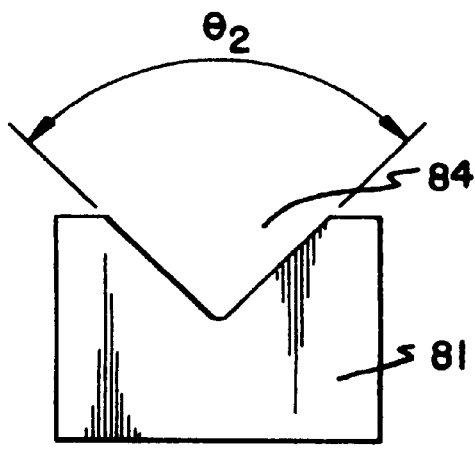
FIG. 19 is a side elevational view of a second electrode for cutting slots in a thin-walled tube as shown in FIG. 17.

As shown in FIG. 19, a second electrode 81 would be generally rectangular in shape with a triangular notch 84. The triangular notch 84 would have a depth that is less than the radius of the tube 50 and an angle $\theta_2$ that is more than 90°, preferably 94°. Because the depth of the triangular notch 84 is less than the radius of the tube 50, a portion of the tube 50 will extend beyond the second electrode 81 as shown in FIG. 17 and will not be cut.

In the preferred embodiment, a second pair of first and second electrodes (not shown) would be oppositely disposed from the first and second electrodes 80, 81 shown in FIG. 17. First, the tube 50 would be secured on both ends. Then, the first pair of electrodes would be plunged into the tube 50 to cut half of a pair of slots 52 as shown in FIG. 17. Then, the first pair of electrodes would be removed and the second pair of electrodes would be plunged into the tube 50 to complete the creation of the pair of slots 52 as shown in FIG. 17. Those skilled in the art would recognize that multiple pairs of electrodes 80, 81 could be displaced along the length of the tube 50 to cut a predetermined pattern of multiple slots 52 in the tube 50 without having to translate either the tube 50 or the electrodes 80, 81. Those skilled in the art would also recognize that other electrode configurations could be used to cut other patterns of slots in the tube 50. Moreover, those skilled in the art would recognize that a laser or other suitable slot cutting tools such as wet chemical and acid etching tools could be used with the present invention.

In other embodiments, the slots or apertures may be cut completely or partially through the tubing wall 50 of a tubular element by wet chemical and acid etching techniques or "chemical milling" to produce structures including slotted hypotubes. Such slots or apertures could also be referred to as "slits", "notches" or "etches." The slots or apertures could also have a variety of shapes which may be suitable such as round, square or rectangular. "Chemical milling" involves coating a stainless steel or nitinol tube with a layer of a positive or negative photoresist material, exposing and developing selected portions of the photoresist material layer, cutting the slots in the tube with chemicals in a chemical etching solution, and removing the remaining photoresist material (and other coating materials if present). Alternate chemical milling methods involve coating a stainless steel or nitinol tube with a layer of chemically resistant material, cutting the slots in the tube with chemicals in a chemical etching solution, and removing the remaining chemically resistant material (and other coating materials if present).

Figure 21A:
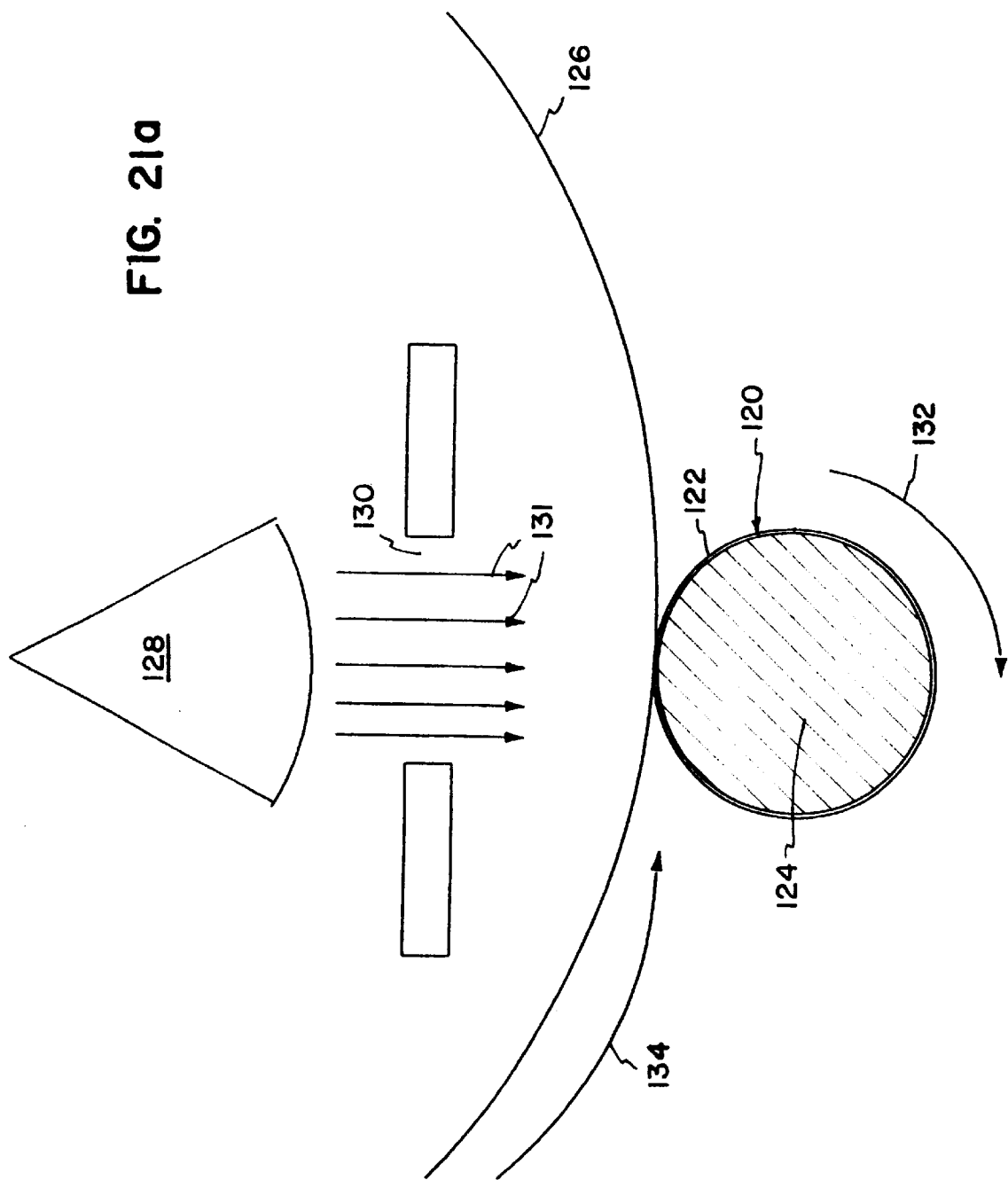
Figure 21B:
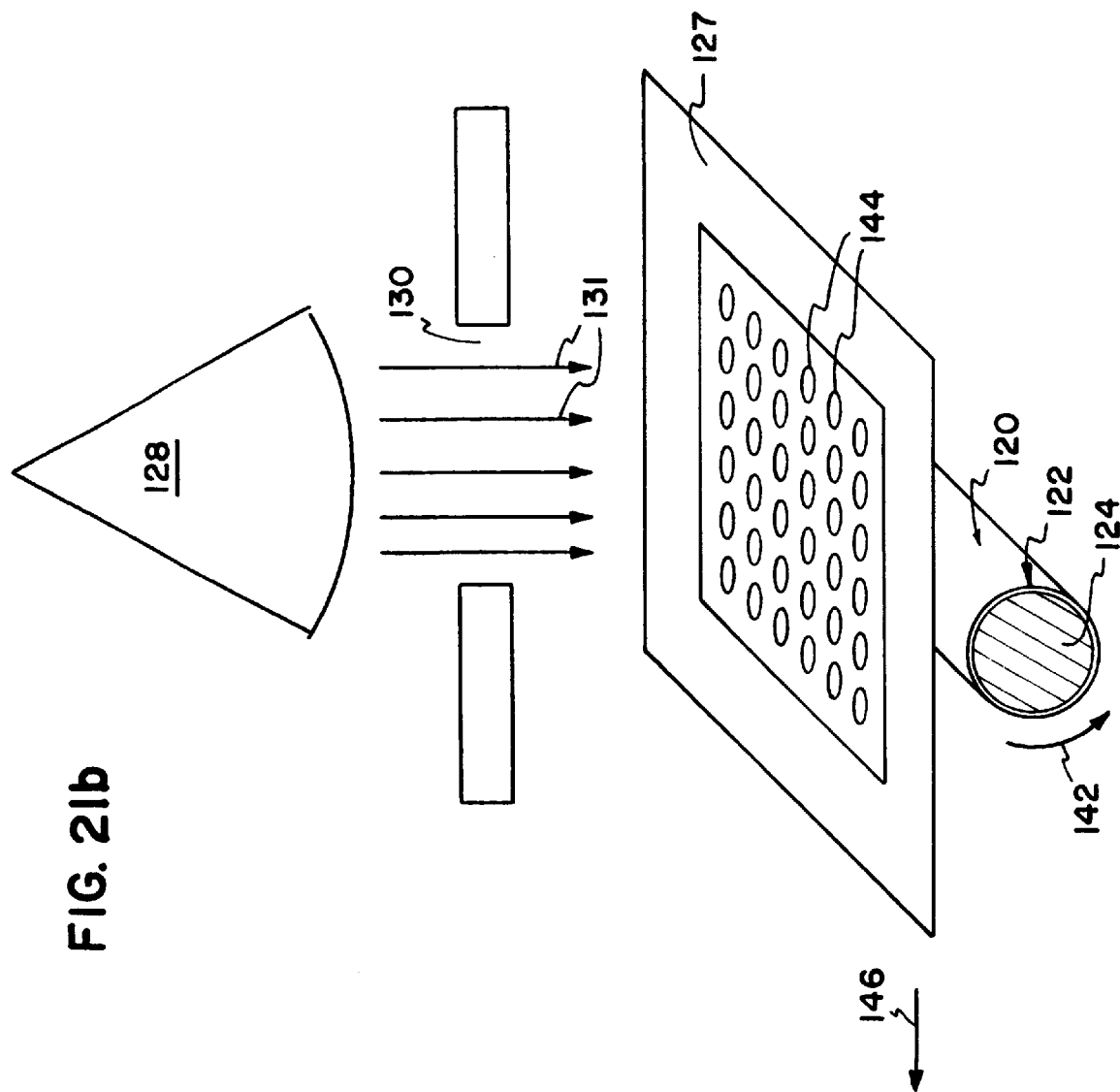

As shown in FIGS. 21a and 21b, there is a first manufacturing process for preparing a tube 120, prior to the photoresist layer being developed and slots chemically milled into the tube. The tube 120, preferably a thin-walled tube, coated with a layer of photoresistive material 122, is positioned on a mandrel 124, or other rotatable tube holding structure. This tube 120 is arranged in close proximity to pattern masks (e.g., photographic film tools) 126 (FIG. 21a), 127 (FIG. 21b), in conjunction with a light source 128 that is controlled by passing through an aperture 130. The light source 138 provides light (indicated by arrows 131), at a wavelength sufficient to expose the photoresistive layer 122 at selected locations.

The photoresistive layer 122 typically includes positive or negative photoresistive polymers commonly known in the art. Some positive photoresistive polymers that may be used are Novolak® based materials such as Photoposit® 111 Photo Resist, Photoposit® 119 S Photo Resist and Photoposit® SP 20–29 Photo Resist, all available from Shipley Company, Inc., 500 Nickerson Road, Marlborough, Mass.

01752. Some negative photoresistive polymers that may be used are KTFR Negative Photoresist, from KTI Chemicals Incorporated, 2 Barnes Industrial Park Road, Wallingford, Conn. 06492. These positive or negative photoresistive polymers are applied to the tube 120 by techniques such as spraying, vapor deposition, or dip coating, as well as other conventional coating techniques known it the art.

The light from the light source 128 is preferably columnated and of a wavelength between approximately 350–400 nm, but may be varied depending on the particular photoresistive material employed. The light may be controlled by a shutter, subject to manual or automated (computer) control.

The photoresist coated tube 120 is patterned or "printed" as the tube 120 is rotated on the mandrel 124 (in the direction of arrow 132). Simultaneously (as shown specifically in FIG. 21a), the pattern mask 126 having apertures (not shown) is translated across the photoresist coated tube 120 in an arcuate path (in the direction of arrow 134). The arcuate path allows the flat pattern mask 126, corresponding to the slots 52 or apertures on the finished tube 50 (FIG. 17)(including areas where tube portions are to remain), to be applied to the rounded surface for creating a pattern on the tube 120.

Alternately (as shown specifically in FIG. 21b), the photoresist coated tube 120 could be rotated as the mandrel 124 rotates (in the direction of arrow 142), as the flat pattern mask 127 having apertures 144, is moved laterally (in the direction of arrow 146). The rotating of the mandrel 124 and the photoresist coated tube 120, coupled with movement of the screen 144 is coordinated such that a portion of the photoresist layer is exposed for creating a pattern on the tube 120, that corresponds to the slots or the apertures of the finished tube 50 (FIG. 17)(including areas where tube portions are to remain). This procedure is repeated throughout the length of the tube 120, to create a pattern for the slots over the entire length of the tube 120.

As shown in FIG. 21c, there is a alternate embodiment to this first manufacturing process for preparing a tube 120, prior to the photoresist layer being developed and slots chemically milled into the tube. This alternate embodiment involves contact between the pattern mask, preferably a photographic film tool, and the photoresist coated tube, along a partial arc (greater than 0° and less than 360°), as opposed to the point contact, illustrated in FIGS. 21a and 21b and detailed in accordance therewith, above.

Tube 120, coated with either positive or negative photoresist 122, as described above by the methods described above, is positioned on the mandrel 124, or other rotatable tube holding structure. This tube 120 is arranged in close proximity to pattern masks (e.g., photographic film tool 326) in conjunction with a light source 128, identical to that described in FIGS. 21a and 21b above.

The film tool 326 is bent downward over the tube 120 and is held in this downward bend on a print frame 328 by blocks 330 and vacuum suction lines 332. It is preferred that the film tool 326 have a pattern of apertures along a partial arc A—A. This partial arc A—A is at least the minimum partial arc in contact with the tube 120, that when the light source 128 is activated, will expose a corresponding arc on the tube, for creating a pattern on the tube 120 (detailed below). Preferably, arc length A—A, having the pattern thereon, extends for approximately 40° to 190°, and in particular, between approximately 50° and 100°, and more particularly, between approximately 60° and 90°.

The photoresist coated tube 120 is patterned or "printed" as the tube 120 is rotated either clockwise or counterclockwise on the mandrel 124 in either a single (360°) rotation or multiple rotations, in a single direction, of preferably equal arcs (corresponding to the partial arc contact A—A between the film tool 236 and the tube 120. The light source 128 is activated during the single rotation as well as during each of the multiple rotations, such that the photoresist layer 122 is exposed for creating a pattern on the tube 120, that corresponds to slots or the apertures of the finished tube (including areas where tube portions are to remain).

Alternately, if a greater partial arc contact (A—A) is desired, the film tool 326 could be clamped to the print frame 328 at points above the blocks 330.

In another alternate embodiment (not illustrated), similar to that shown and described in FIG. 21c, a pattern mask, preferably a photographic film tool (film tool), that is of a sufficient rigidity to be curved, such that the curvature contacts a photoresist coated tube along a partial arc, the contact being similar to that described in FIG. 21c above. The photoresist coated tube (with positive or negative photoresistive material) is prepared in accordance with the methods disclosed above, and is positioned on a mandrel or other similar rotatable tube holding structure, as described above. The pattern mask is placed intermediate the photoresist coated tube and the light source (similar to that disclosed in FIGS. 21a–21c above), and particularly the photoresist coated tube is within the curvature of the photographic film tool, with contact along a partial arc greater than 0° and less than 360°, preferably between 45° and 270°, and most preferably, approximately 180°.

The photoresist coated tube is patterned or "printed" as the tube is rotated on the mandrel, preferably in a clockwise direction, and the film tool is translated (advanced) along a substantially linear path (left to right due to clockwise rotation of the tube), the linear advancement being coordinated with the rotation of the tube, to maintain the curvature of the film tool, to allow for continuous contact over the partial arc. The film tool is advanced preferably by a motor driven mechanism and is movably engaged on a frame (similar to the frame 328 shown in FIG. 21c). The pattern mask (film tool) includes apertures (not shown) preferably along its length, this length of apertures (not shown) preferably along its length, this length of apertures being coordinated with the circumference of the tube, such that the tube, once exposed by the activated light source, is exposed with a pattern that will result in corresponding slots 52 or apertures on the finished tube 50 (FIG. 17)(including areas where tube portions are to remain). The rotations of the tube with accompanying film translations could be achieved by a single rotation and accompanying translation, or multiple rotations and accompanying translations, provided the rotation(s) and accompanying translation(s) were coordinated with the light source activation(s), such that preferably, exactly the 360° arc of the tube was patterned.

Figure 22:
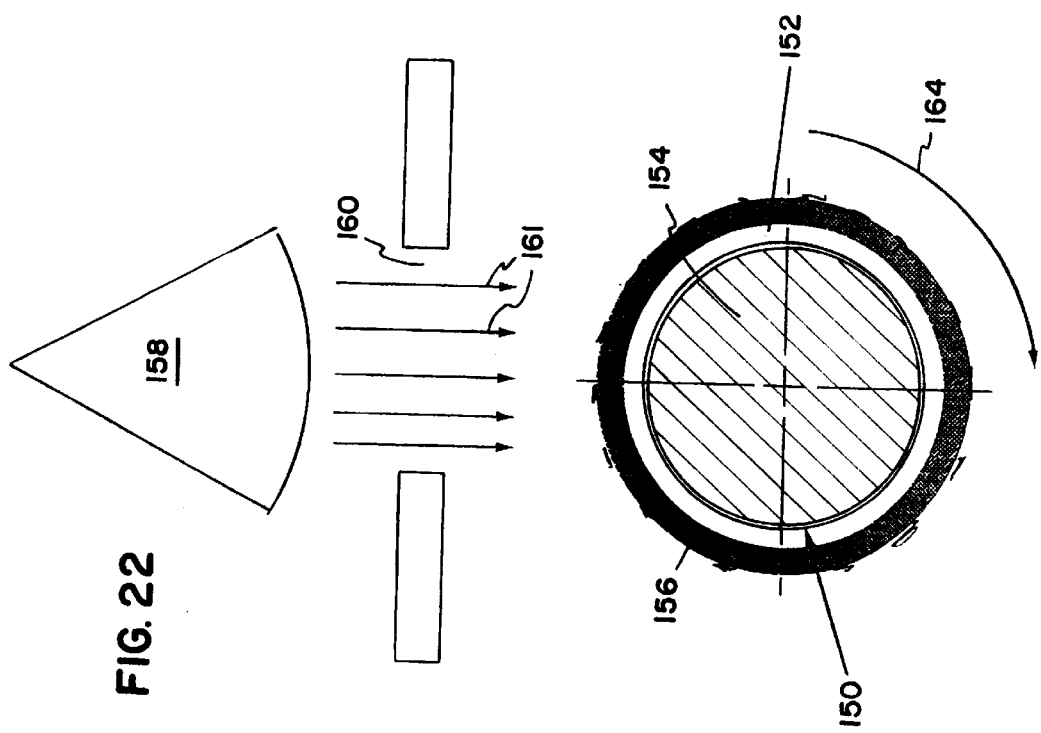
FIG. 22 is a side view of an alternate manufacturing method for creating slots in a thin-walled tube as shown in FIG. 17.

FIG. 22 shows a second manufacturing process for preparing a tube, preferably a thin-walled tube, prior to the photoresist layer being developed and slots chemically milled into the tube. The tube 150, coated with a layer of photoresistive material 152, as described above, is positioned on a mandrel 154, or other rotatable tube holding structure. A mask (phototool) 156, preferably in the form of a glass tube having a pattern written (printed) onto its inner or outer surface, is then placed concentrically over the tube 150. This mask 156 has an inner diameter slightly larger than the outer diameter of the tube 150 so the photoresist coated tube 150 can fit snugly within the mask 156. This tube 150 is arranged in close proximity to a light source 158 that is controlled by passing through an aperture 160. The light source 128 provides light (indicated by arrows 161), preferably columnated, at a wavelength sufficient to expose the photoresistive layer 152 at selected locations (corresponding to the slots or apertures of the finished tube, including areas where tube portions are to remain), as the tube 150 is rotated exactly together with the mask 156 (in the direction of arrow 164).

An alternate embodiment (not illustrated) of the second manufacturing process, detailed above and illustrated in FIG. 22, for preparing a tube, preferably a thin walled tube, prior to the photoresist layer being developed and slots chemically milled into the tube, will now be described. Accordingly, for the machinery and structures involved with this alternate embodiment, reference should be made to FIG. 22 and its description immediately above. In this alternate embodiment, the tube is identical to tube 150 above, and is coated with a photoresistive layer (positive or negative) as described above, and is placed on a mandrel or other tube holding structure, identical to that disclosed above.

The mask (phototool), preferably in the form of a glass tube, is different from that described above, as it preferably has a pattern written (printed) onto a portion or arc (less than 360°) of the glass tube, but could have a pattern printed over the full arc (360°). Additionally, the glass tube is stationary and of a larger inner diameter than the outer diameter of the photoresistive material coated inner tube, allowing for the photoresist coated (inner) tube to be rotated, in partial (less than 360° rotation) or full (at least 360°) rotations within the glass tube mask. It is preferred that the glass tube mask have a pattern printed along an arc from approximately 45° to 225°, with approximately 60°, 90°, 120° and 180° arcs being preferred.

The photoresist coated tube, within the stationary glass tube mask, preferably concentrically, is arranged in close proximity to a light source, preferably columnated and identical to the light source 158 disclosed above. The photoresist coated inner tube is then rotated (clockwise or counterclockwise, provided all rotations are in the same direction) at rotations corresponding to the arc (e.g., 60°, 90°, 120° and 180°) patterned onto the outer stationary glass tube mask. The light source is preferably activated upon each rotation and deactivated upon the termination of each rotation. However, the rotation can be continuous, covering the entire 360° arc if desired, whereby, the light source would not be deactivated. As described above, the light source is of a wavelength sufficient to expose the photoresistive coating on the inner tube at selected locations, corresponding to the slots or apertures of the finished tube (including areas where tube portions are to remain).

Figure 23A:
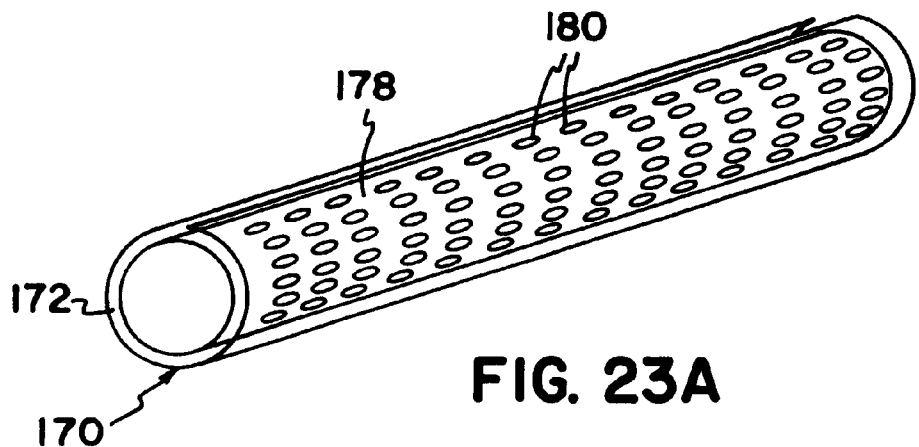
FIGS. 23a and 23b are perspective views of thin-walled tubes prepared for exposure to light prior to being developed.
Figure 23B:
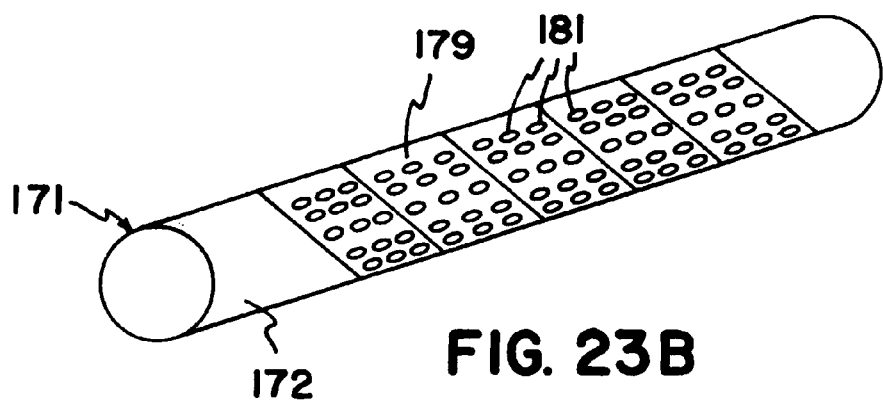

FIGS. 23a and 23b show a third manufacturing process for preparing the preferably thin-walled tubes, prior to the photoresist layer being developed and slots chemically milled into the tube. The tubes 170, 171 are initially coated with a layer of photoresistive material 172, as described above. Pattern masks (phototools), in the form of films 178, 179 with apertures 180, 181 (corresponding to the slots or apertures to be cut into the finished tubes), are wrapped around the photoresist coated tube 170. The films 178, 179 could be a sheet 178 or series of sheets attached to the photoresist coated tube 171 (FIG. 23a) or a strip 179 wrapped around the photoresist coated tube 170 (FIG. 23b). Once the films 178, 179 are secured to the respective photoresist coated tubes 170, the photoresist coated tubes 170, 171 would be positioned on the mandrel 154 (FIG. 22) or other similar rotatable tube-holding structure, and processed in accordance with the above disclosed second manufacturing process that is detailed in FIG. 22.

Figure 24:
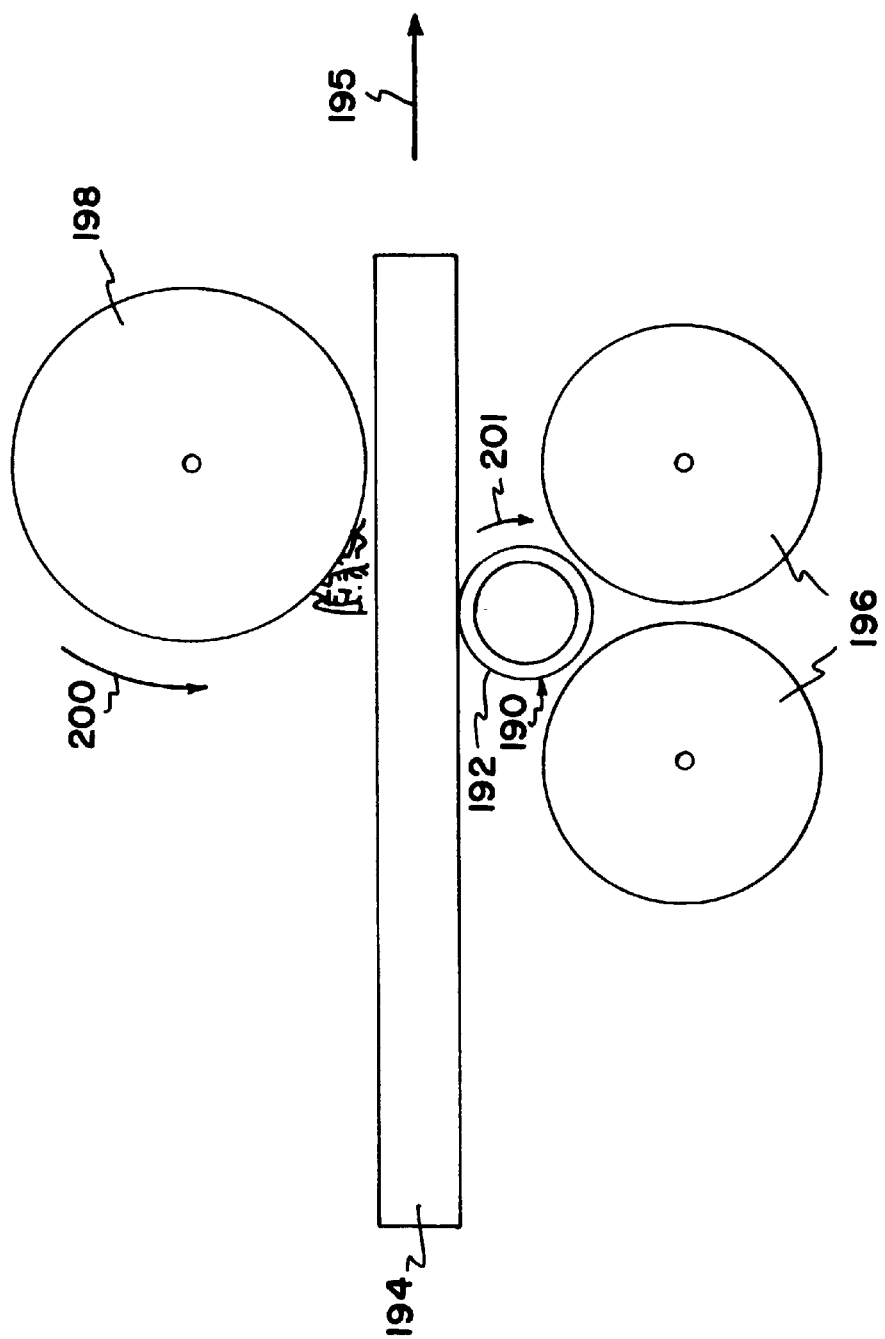
FIG. 24 is a side view of a method for screen printing a mask onto a photoresist coated thin-walled tube.

FIG. 24 details a fourth manufacturing process for preparing the tube prior to the photoresist layer being developed and slots chemically milled in to the tube. The tube 190 is initially coated with a layer of photoresistive material 192, as described above. This photoresist coated tube 190 is then placed between an upper screen 194 (moveable laterally in the direction of arrow 195) and lower support rollers 196. An roller 198 (rotating in the direction of arrow 200), coated with chemically-resistant ink, preferably acid resistant ink, is positioned above the screen 194.

The movement of the screen 194 is coordinated with the rotation of the ink coated roller 198 such that ink is forced through apertures (not shown) in the screen 198, rotating the tube 190 (in the direction of arrow 201), resulting in the entire photoresist coated surface 192 of the tube 190 being correctly patterned. The pattern corresponds to the slots or apertures of the finished tube, as the inked portions of the photoresist coated tube serve as the mask. The photoresist coated tube 190 can then be placed on a mandrel 154 (FIG. 22) or other similar tube holding structure and processed in accordance with the second manufacturing process disclosed above and detailed in FIG. 22. Alternately, this inked pattern could be applied by laser printing or ink jet printing (described below).

There is a fifth manufacturing process (not illustrated) for preparing the tube prior to the photoresist layer being developed and slots chemically milled into the tube. The tube is coated with a layer of photoresistive material, as described above. This photoresist coated tube is then placed inside of a stationary glass tube that serves as a mask (phototool), as this stationary tube includes a pattern of pin-hole apertures. This stationary glass tube mask is arranged in close proximity to a light source. As the photoresist coated tube is rotated, the light source is activated at predetermined times, corresponding to predetermined rotational locations of the photoresist coated tube. This action exposes the photoresist coated tube at locations corresponding to the slots or apertures of the finished tube.

Once the photoresist coated tubes are prepared by any of the above methods, these tubes, coupled with their respective masks, could also be exposed by being subjected to laser radiation as a substitute for the above disclosed light sources. For example, the laser radiation could be from an excimer laser or ultraviolet (UV) laser, to expose predetermined locations on the tube. The exposed locations would correspond to the slots or apertures of the finished tube (including areas where tube portions are to remain). Moreover, laser radiation may be applied directly to non-masked photoresist coated tubes, exposing the tubes at predetermined locations, corresponding to the slots or apertures of the finished tube (including areas where tube portions are to remain).

The exposed tubes (having the photoresistive material coating exposed such that either areas where the slots or apertures are to be, or areas where tube portions are to remain) are then developed as either a positive or a negative, with suitable developers depending on the photoresistive material employed. For example, if positive photoresistive materials, such as Photoposit® 111, 119 S, or SP 20–29 (all disclosed above) are employed, Photoposit® 303 A Developer, available from Shipley Company, Inc., 500 Nickerson Road, Marlborough, Mass. 01752 may be the developer. For example, if the negative photoresistive material KTFR Negative Photoresist (disclosed above) is employed, KTFR Developer, available from KTI Chemicals Incorporated, 2 Barnes Industrial Park Road, Wallingford, Conn. 06492 may be used. The pattern of photoresist material on the tube is such that the tube is now suitable for further processing and development. The developed tube may now be chemically milled, preferably by placement in an acid bath for chemical etching.

The chemical etchant is preferably an acid etchant, such as ferric chloride of a photoengraver's grade at 36–42 degrees Baume in a bath at approximately 125 degrees F. Other etchants include solutions of ferric chloride and hydrochloric acid, a five volume solution of one volume concentrated hydrochloric acid (37%), one volume concentrated nitric acid (70%), and three volumes of water, this etchant under similar conditions as above, and Ferric Chloride at approximately 42 degrees Baume at approximately 130 degrees F. (hydrochloric acid may be added). The tube is removed from the bath after approximately thirty seconds to ten minutes and the time depends on the depth and width of the slots desired, as well as the thickness of the metal substrate (i.e., the tubular element). (Under these conditions, stainless steel etches at approximately 0.5 mm/minute). Alternately, the tube can be removed from the bath, proximal end first, followed by its distal end. This allows the acid additional time to etch at the distal end, such that the slots cut at this end will be wider, giving the distal end greater flexibility than the proximal end.

Greater flexibility at the distal end of the tube (as opposed to the proximal end) can also be achieved by employing the above disclosed masks having patterns with the portions that correspond to the locations of the chemically milled slots (of the finished tubes) being closer to each other at the distal end. Upon conclusion of a chemical etch (disclosed above), the slots at the diital end are closer to each other than the slots at the proximal end. Moreover, the above disclosed masks may be patterned such that the resultant apertures are; 1) of the same size but spaced apart from each other at different lengths, preferably as described above, 2) of different sizes throughout the length of the mask but spaced equidistant from each other, in particular of different, preferably larger, sizes at areas of the mask corresponding to the distal end of the finished tube (as opposed to the proximal end of the finished tube), or 3) of different shapes (e.g., round, square, rectangular, polygonal, and/or combinations thereof, as described above), of the same or different size and spaced apart from each other at either the same or different lengths.

The photoresistive material (as well as other materials such as inks) that remains on the tube is then removed by techniques such as stripping with chemicals compatible with the positive or negative photoresistive materials remaining on the tube. For example, if positive photoresistive materials, such as Photoposit® 111, 119 S, or SP 20–29 (all disclosed above) are employed, Photoposit® Remover 1112A, available from Shipley Company, Inc., 500 Nickerson Road, Marlborough, Mass. 01752 may be used to strip the remaining photoresist (as well as other material remaining on the tube). For example, if the negative photoresistive material KTFR Negative Photoresist (disclosed above) is employed, Products 13/LS, 14/HS, 14/KS and ICL/8000, all available from Photofabrication Chemical and Equipment Company, 522 Route 30, Frazier, Pa. 19355 may be used to strip the remaining photoresist from the tube. Other strippers may be added to stripping mixture to remove other materials, such as inks, that may also be remaining on the tube. These other strippers may be compositions such as, Products 68, SS1, THP, GPS and PRS-3, all available from Photofabrication Chemical and Equipment Company, 522 Route 30, Frazier, Pa. 19355. Alternately, other photoresist stripping techniques, well known to those skilled in the art, could also be used to remove the photoresist and any other material remaining on the tube.

In an alternate embodiment of chemical milling, the chemically resistant material, such as the photoresistive materials disclosed above, as well as other acid resistant materials, could be coated onto the stainless steel or nitinol tube in a pattern conforming to the slots or apertures to be cut, by methods such as ink jet printing or screen printing.

Figure 25:
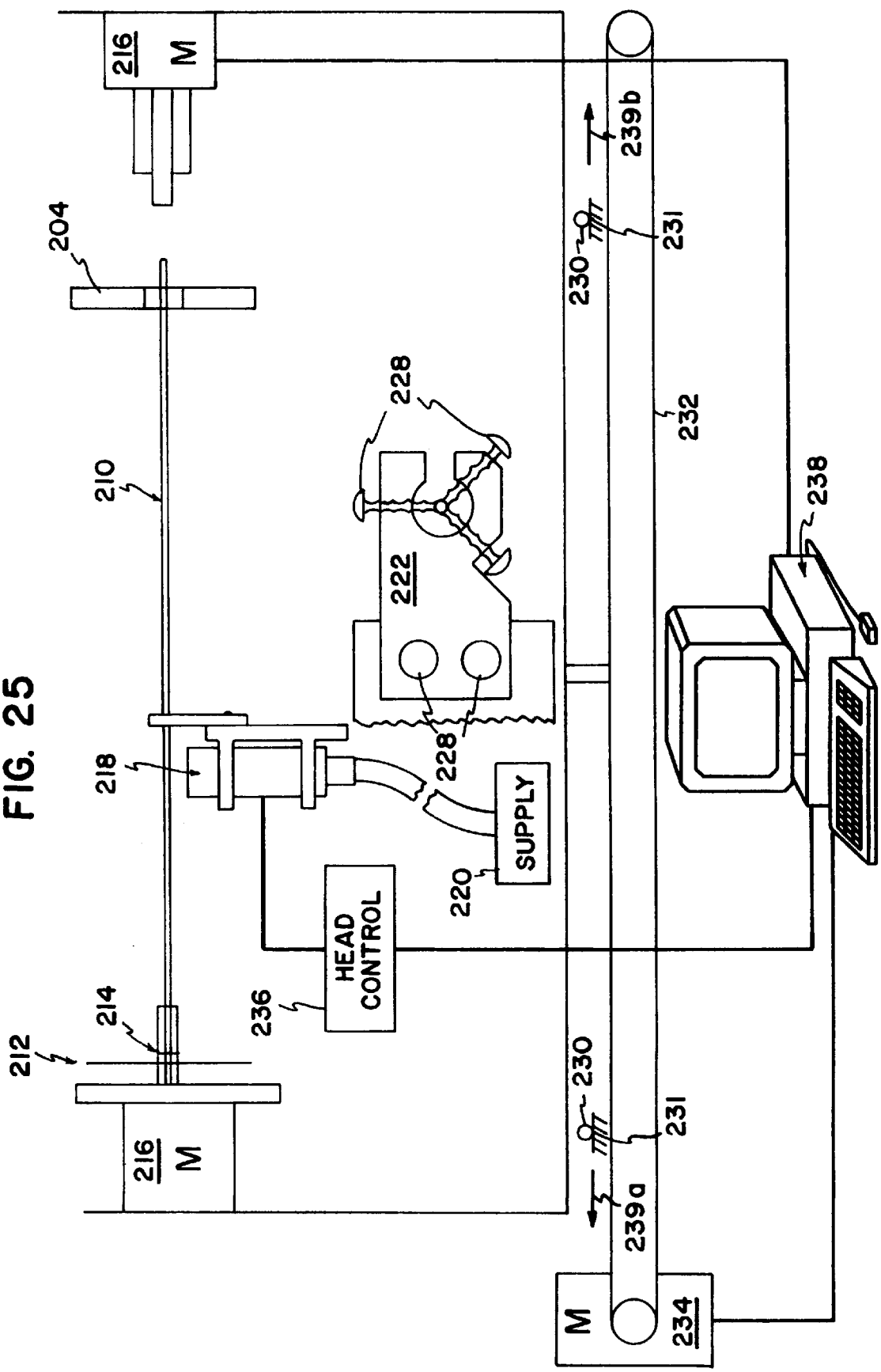
FIG. 25 is a side view of a method for printing a photoresistive material layer onto a thin-walled tube.

FIG. 25 details an automated, computer controlled, ink jet printing method for applying chemically resistant material to a tube 210 in a predetermined (preprogrammed) pattern, corresponding to the slots or apertures to be cut partially therein or completely therethrough. The tube 210 is held on a print lathe 212 by collets 214. Motors 216 on the lathe 212 drive the collets 214, such that the tube 210 is rotated. The lathe 212 also includes a print head 218, through which the chemically resistant material, from a supply 220, is printed onto the tube 210. A guide 222 on the print head 218 (FIG. 25) as well as secondary guide(s) 224 (only one shown) on the lathe 212 maintain the tube 210 in the proper position. The guide 222 on the print head 218 is attached thereto by bolts 226. Screws 228, preferably made of plastic, extend laterally through the guide 222, and serve to retain the tube 210 in the proper position during printing.

The lathe 212 is mounted on wheels 230, the wheels being received on lands 231. The lathe 212 is also attached to a belt 232 or other equivalent carriage. The belt 232 is driven by a motor 234. All of the motors 216, 234 and the head control 236 for the print head 218 are preferably controlled by a computer 238 or other similar microprocessor. The belt 232 moves to translate the tube 210 as the chemically resistant material is patterned onto the rotating tube 210. The preferred translation distance is approximately one meter in both directions (represented by arrows 239a, 239b) so that the entire tube can be printed. Printing can be in one or both directions, depending upon the length of the tube.

This method could also be used to place an inked pattern, corresponding to slots or apertures of the finished tube, onto a photoresist coated tube (the photoresist coated onto the tube by spraying, vapor deposition, dip coating etc., as disclosed above). The ink would be applied as a light (radiation) blocking layer onto the photoresistive material coating from the print head 218 of the lathe 212, in accordance with a computer controlled pattern. The photoresist coated tube would then be exposed by the light sources or laser radiation, as disclosed above. The exposed tubes would be developed, in accordance with the procedures disclosed above, and chemically milled in accordance with the chemical etching methods disclosed above.

This method could also be used with a tube to make a tubular mask (phototool), such as the mask 156 in FIG. 22. In this case, the tube would be processed similar to that described above, except masking material (i.e., ink) would be placed into the supply 220, such that the print head 218 would print this masking material onto the tube.

Slots are then cut into the tube by chemical milling, as the coated patterned tube is chemically etched by placement into the bath of acid etchant described above, in accordance with the methods described above. Once the chemical etch is complete, the chemically resistant material (and any other materials, e.g., ink) remaining on the tube is removed by the stripping processes described above. The tube may then be encased in a suitable low friction material, as described above, to seal off the slots (if cut completely through the tube) making the tube fluid tight.

In another embodiment, that may be used to produce slotted hypotube, slots or apertures are cut into a tubular element (tube) by a process referred to as laser ablation. In this process, the tube is coated with a chemically resistant material, such as Teflon® or polyimide. A pattern of apertures would then be made in the coated tube as radiation (light) from a laser would ablate or burn off portions of the chemically resistant material coating, corresponding to the slots or apertures of the finished tube. The tube would then be chemically milled by chemically etching the tube in an acid etchant bath, as described above, in accordance with the methods described above. Slots at the distal end of the tube could be cut wider and/or closer together than those at the proximal end of the tube, to provide the tube with greater flexibility at the distal end. The remaining coating material would then be stripped by conventional techniques. Additionally, a laser may be used to cut the slots or apertures directly into the tubular element, either partially or completely therethrough, in various shapes and sizes.

In some embodiments, the slots 52 or apertures need not be cut completely through the tubing wall 50. Such apertures could also be referred to as "slits", "notches" or "etches." The apertures could also have a variety of shapes which may be suitable such as round, square or rectangular apertures. It will be appreciated that the flexible tubular member 20 might be manufactured in any number of ways in keeping with the principles of the invention. For example, holes of a suitable pattern might be cut in a flat sheet of material such as stainless steel or nitinol which is then rolled and welded into the appropriate shape. In yet other methods, holes of a suitable pattern might be cut in a thicker, shorter tube of metal which is then drawn into an appropriate shape.

Figure 6:
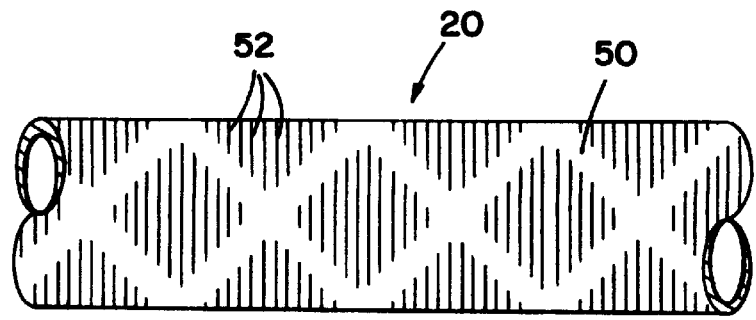
FIG. 6 is a partial side elevational view of an alternate embodiment of a catheter, guidewire, catheter sheath or drug infusion catheter/guidewire in accordance with the principles of the present invention wherein slots are cut into a wall of a thin walled tube.
Figure 7:
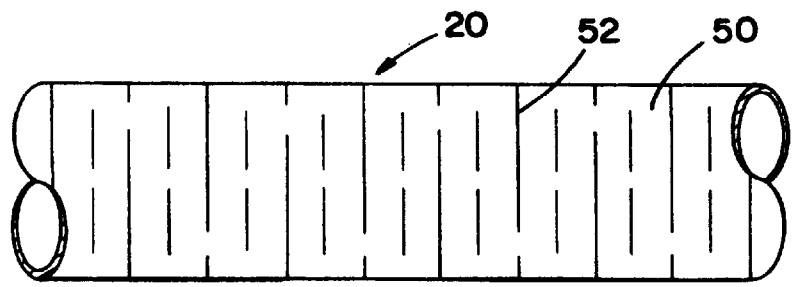
FIG. 7 is a view similar to FIG. 6 illustrating the slots being spaced further apart.
Figure 8:
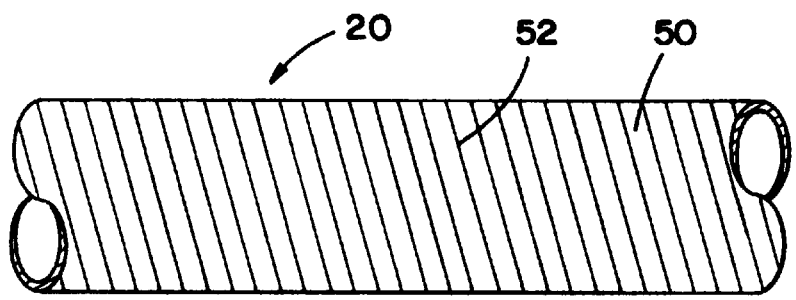
FIG. 8 is a view similar to FIG. 7 illustrating the slots being spaced closer together and continuous.

In FIGS. 6–8 the slots are shown as running generally transverse to the longitudinal axis of the flexible tubular member 20. The flexible tubular member 20 shown in FIG. 6 is more flexible than the flexible tubular member 20 shown as FIG. 7 as the slots 52 are closer together. One example of the spacing between slots is 0.05 to 0.10 inches. The flexible tubular member 20 of FIG. 8 has a continuous slot (of plural apertures) in a spiral and is very flexible.

Figure 9:
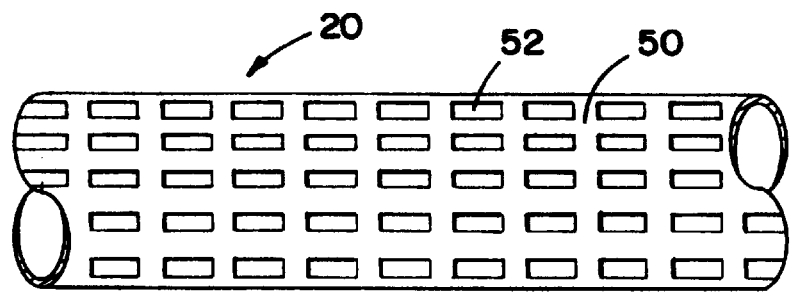
FIG. 9 is a partial side elevational view of a catheter, guidewire, catheter sheath or drug infusion catheter/guidewire in accordance with the principles of the present invention wherein longitudinally extending slots have been cut into the catheter, guidewire, catheter sheath or drug infusion catheter/guidewire.
Figure 10:
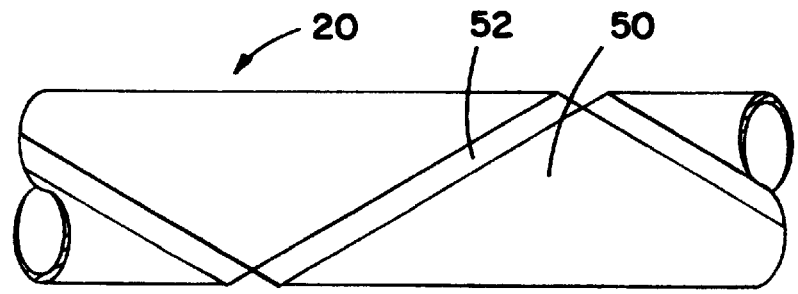
FIG. 10 is a view similar to FIG. 9 illustrating an alternate embodiment of a catheter, guidewire, catheter sheath or drug infusion catheter/guidewire wherein a helical slot has been cut in the wall of the catheter, guidewire, catheter sheath or drug infusion catheter/guidewire.

In FIG. 9, an alternate embodiment is shown wherein the slots 52 extend longitudinally of the tube 50. In FIG. 10, a slot 52 is shown as extending helically about the tube 50. It will be appreciated that any number of different slot configurations might be created in the tube 50. Moreover, the configuration of the slots might be varied along the length of the tube 50 so as to provide a flexible tubular member 20 with varying characteristics along its length.

A further explanation of the invention for use as a catheter, including a guide catheter or balloon catheter, a guidewire, a catheter sheath or drug infusion catheter/ guidewire is provided hereinafter.

Catheters

As described earlier, the various embodiments of the invention can be used as catheters. The inside and outside diameters of the catheters may vary, however, some catheters have an outside diameter from 0.010 inches to 0.250 inches or larger. The use of the invention as a catheter is particularly advantageous because one can make a catheter having varied characteristics along its length. For example, the distal end of the catheter typically must be very flexible, while other areas of the catheter must be stiffer to provide the longitudinal stiffness to transmit the torque required to maneuver the catheter. These requirements can be met by varying the windings of the coils 21 or by welding adjacent windings of the coil 21 as described in the first embodiment of the invention or by varying the configuration of the slots 52 in the flexible tubular member 20 as described in the second embodiment of the invention.

Figure 11:
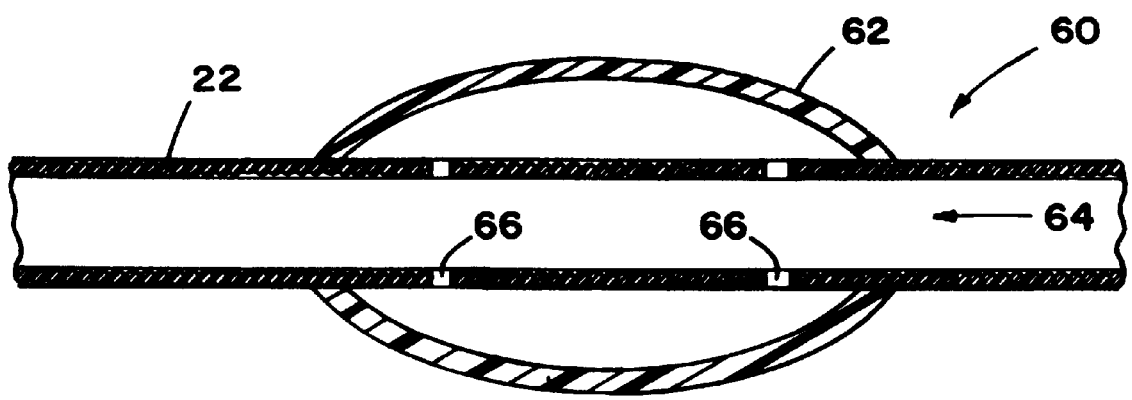
FIG. 11 is a sectional view of a balloon catheter comprising a catheter made from the embodiment shown in FIG. 1.

FIG. 11 illustrates a balloon type catheter 60 utilizing an embodiment of the flexible tubular member 20 for use as a catheter shown in FIG. 1. The balloon catheter 60 includes an expandable balloon portion 62 interconnected to lumen 64 of the catheter 20 by ports 66. The balloon portion is expanded to temporarily obstruct the passageway of a coronary artery or the like during angioplasty treatment.

Guidewires As described earlier, a coated flexible tubular member 20 in accordance with the invention can be used as a guidewire. The guidewires that are currently used are comprised of a core wire that is welded to the inner surface of a spring coil. TEFLON® is then spray coated on the outside of the device to complete the assembly of the guidewire. However, in order to make these guidewires steerable, the core wire has a series of elaborate tapering schemes to vary the stiffness and flexibility of the various portions of the guidewire.

Figure 20:
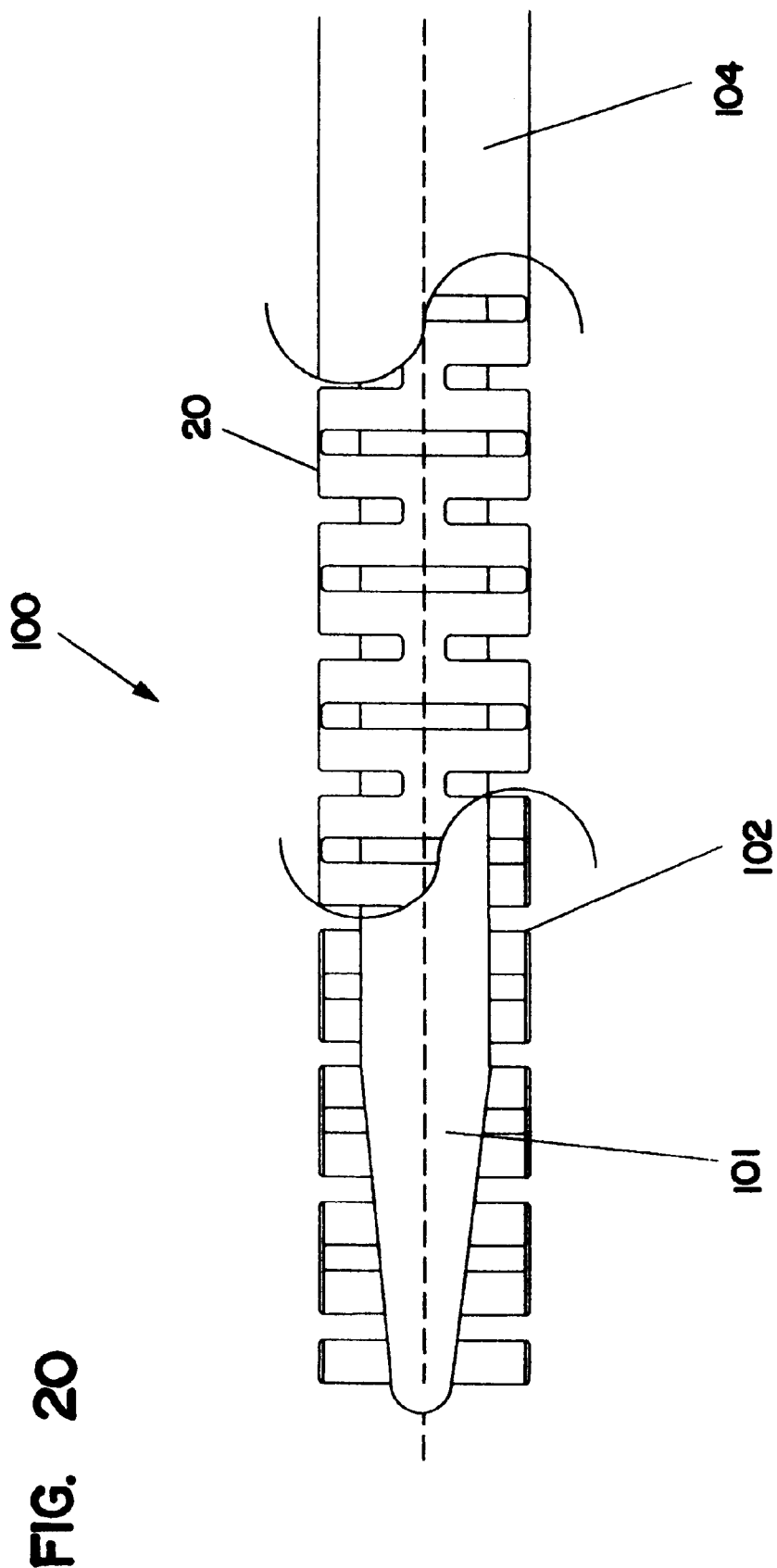
FIG. 20 is a partial cross sectional view of a representative guidewire of the present invention.

As shown in FIG. 20, a guidewire 100 made according to the present invention would be comprised of a core wire 101 that is attached to a flexible tubular portion 20 made according to any of the previously described embodiments of the invention. In FIG. 20, the following configuration is shown by way of example: a core wire 101 attached to the distal end of the guidewire 100 and having a single tapered section; a slotted tubular portion 102; and a coil 103 attached between the core wire 102 and the distal end. The outer surface of the tubular portion 20 is covered with an appropriate biocompatable encasing 104 as described hereinabove. However, various other guidewire configurations could be employed within the scope of the present in invention. For instance, the core wire 101, could have multiple tapered sections or it could be of constant or other variable cross section; it also does not have to be attached at the distal end of the guidewire 100. Other variations known in the prior art could include the addition of a safety ribbon, the elimination of coil 103 (so that the tube extends to the distal end), or the addition of more coiled sections. The length of these guidewires would typically range from 150 centimeters to 300 centimeters and the flexible tubular member 20 would have an outside diameter between 0.010 and 0.065 inches.

By varying the flexibility of the flexible tubular member 20 along the length of the guidewire as described above, a guidewire in accordance with the present invention can achieve the functions of current guidewires without the need for elaborate tapering schemes for the core wire. For example, as described in the first embodiment, the distal end of the guidewire could be made very flexible by using a coil 21 with more longitudinally displaced windings, while the proximal end of the guide wire could be made stiffer by having more circular windings or by welding adjacent windings together. As previously described in the second embodiment, as well as those embodiments produced by Electrostatic discharge machining (EDM) and chemical milling, the same result could be achieved by varying the configuration of the slots 52 in the tube 50.

Figure 26:
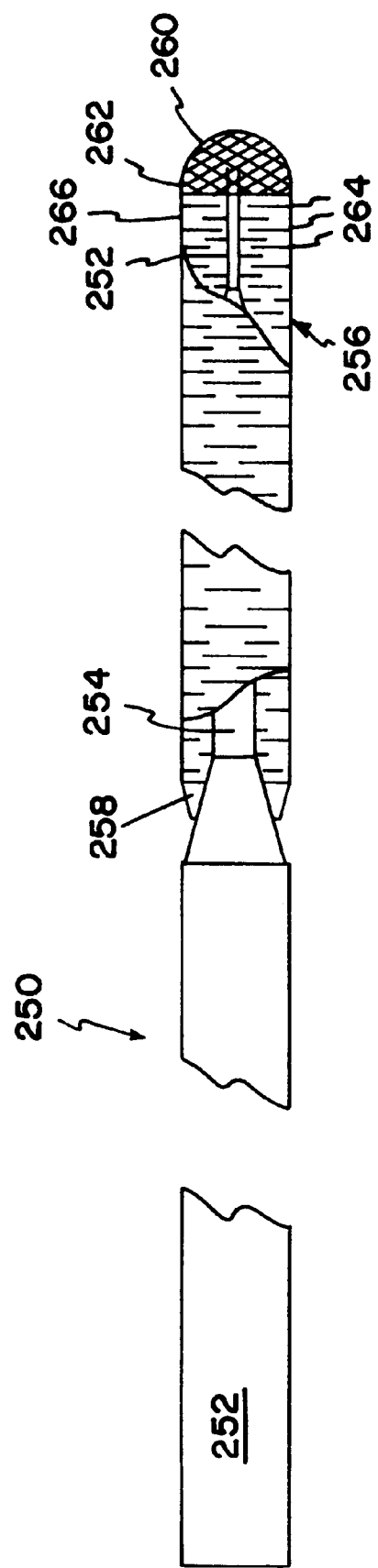
FIG. 26 is a sectional view of a guidewire made with a segment of tubing, made in accordance with the present invention.

FIG. 26 shows a guidewire 250 made with slotted hypotube prepared in accordance with the present invention. This guidewire 250 is formed of a core wire 252 having a tapered distal portion 254. A tubular member 256, preferably made of a slotted hypotube segment in accordance with the invention, is then welded onto the tapered distal portion 254 of the core wire 252 at weld or solder joints 258. A blunt nose piece 260 is formed, preferably by burnishing, at the distal end 262, as the core wire 252 and the tubular member 256 are welded or soldered together. Specifically, the slots 264 at the end of the tubular member 256 at the far distal end 266 of the guidewire 250 are preferably wider than the other slots 264 of the tubular member 256. This configuration provides the guidewire 250 with greater flexibility at the distal end 262.

Catheter Sheaths and Catheter Introducers

As described earlier, a coated flexible tubular member 20 in accordance with the invention could also be used as a catheter sheath. The inside and outside diameter of catheter sheaths may vary to meet different introducer and catheter requirements; however, several embodiments of a catheter sheath have an outside diameter from 0.050 inches to 0.300 inches or larger. As described earlier, catheter sheaths require a high hoop strength at the distal end to prevent burring and notching and flexibility in the center portion to prevent kinking. To meet the requirements, the windings of the coil 21 in the first embodiment of the invention can be varied or welded to provide a high hoop strength at the distal end of the catheter sheath and the center portion of the catheter sheath can be made flexible to prevent kinking. Likewise, the configuration of the slots 52 in the tube 50 of the second embodiment can be varied to produce the same characteristics.

Figure 12:
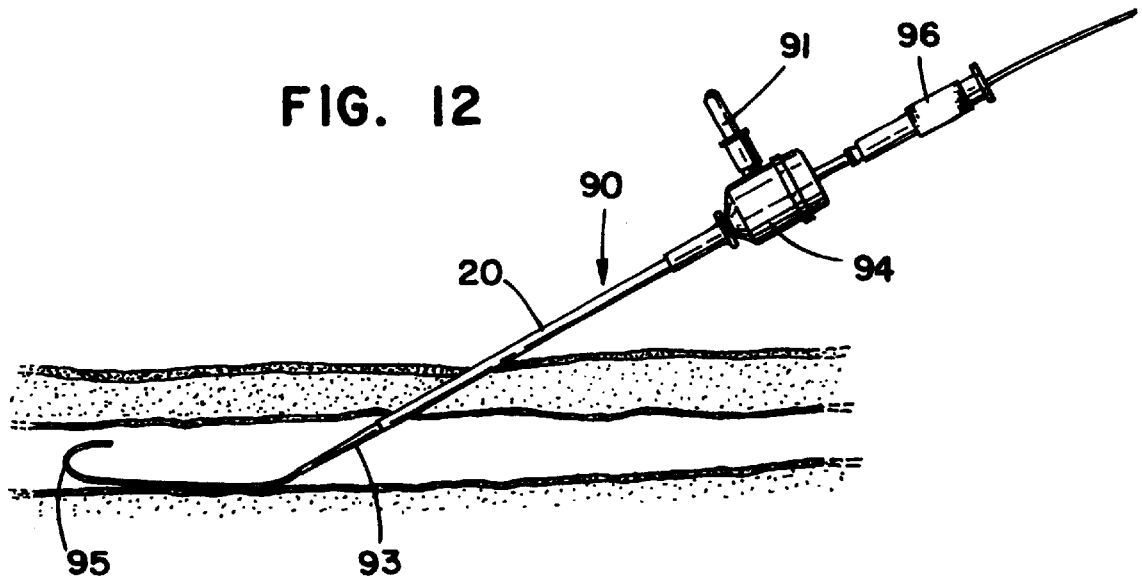
FIG. 12 is an elevational view with portions broken away of a catheter introducer, a guidewire and dilator after they have been advanced into the blood vessel of a patient.
Figure 14:
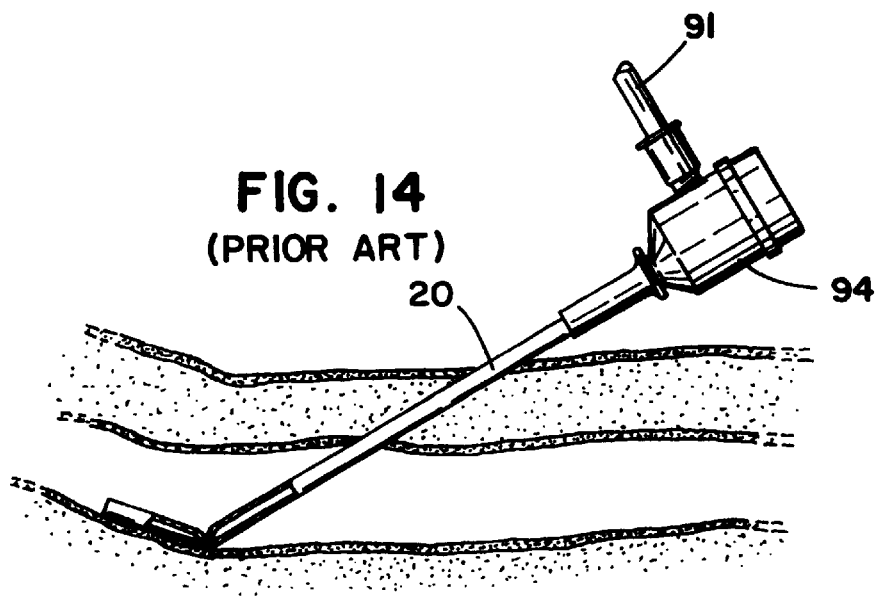
FIG. 14 is an elevational view of a prior art version of a catheter introducer with portions broken away after it has been advanced into a blood vessel of a patient and the dilator unit and guidewire have been withdrawn, showing a kinked catheter sheath.
Figure 13:
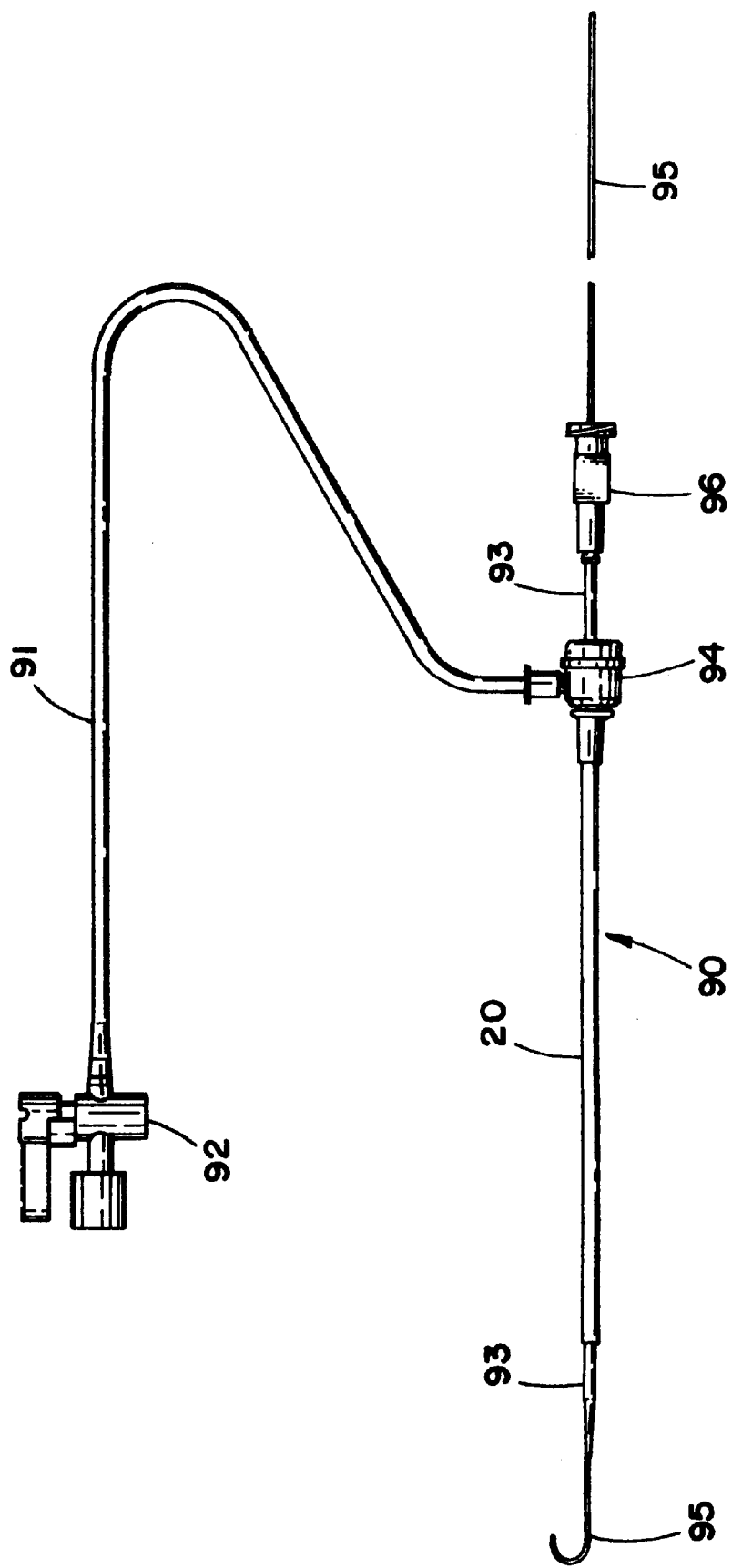
FIG. 13 is an elevational view of the catheter introducer having a fluid introduction tube and having a dilator and guidewire inserted therein.

As shown in FIGS. 12 and 13, a coated flexible tubular member 20 according to the present invention for use as a catheter sheath can be incorporated into a catheter introducer, generally designated as 90. In the preferred embodiment, the introducer 90 would have a hub 94 with hemostasis valve means that is connected to the coated flexible tubular member 20 (catheter sheath) and to a feed tube 91 having a three-way stop cock 92. Those skilled in the art will recognize that any hemostasis valve means such as those disclosed in U.S. Pat. Nos. 4,000,739 and 4,610,665 could be used with the present invention. The feed tube 91 is arranged and configured to allow the insertion of fluids through the hub 94 and catheter sheath 20 and into the patient's blood vessel.

The hub 94 and catheter sheath 20 are also arranged and configured to allow the insertion of a dilator 93 through the lumen of the hub 94 and catheter sheath 20. The dilator 93 would contain a lumen that is arranged and configured to allow the insertion of a guidewire 95 through the dilator 93. In the preferred embodiment, the dilator 93 is generally cylindrical in shape with a tapered distal end and having a stop portion 96 generally located at its proximal end that is arranged and configured to temporarily secure the dilator 93 to the hub 94. The dilator 93 also has an outer diameter that is approximately equal to the diameter of the lumen in the catheter sheath 20 so as to provide an interference fit to support to the catheter sheath 20 during its insertion into the blood vessel. Those skilled in the art would recognize that other dilators 93 could be used with the invention.

Drug Infusion Catheter/Guidewires

Figure 15:
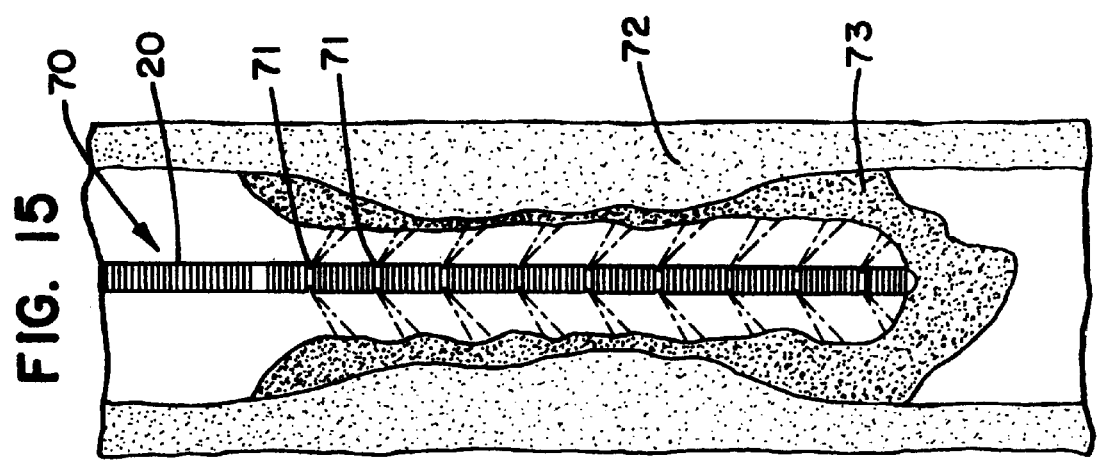
FIG. 15 is an elevational view of a representative guidewire type drug infusion catheter/guidewire with portions broken away after it has been advanced into a blood vessel of a patient and the core has been withdrawn.

As described earlier, drug infusion catheter/guidewires can also be made according to the present invention. As shown in FIG. 15, a guidewire type drug infusion catheter/guidewire 70 is located within the lumen of a blood vessel 72 with occlusion 73. The guidewire type drug infusion catheter/guidewire 70 would be comprised of a flexible tubular member 20 made in accordance with the previously described invention having side holes 71 near its distal end and a removable core wire (not shown). Like guidewires, the flexible tubular member 20 would have a small outside diameter ranging between 0.01 and 0.05 inches.

Figure 16:
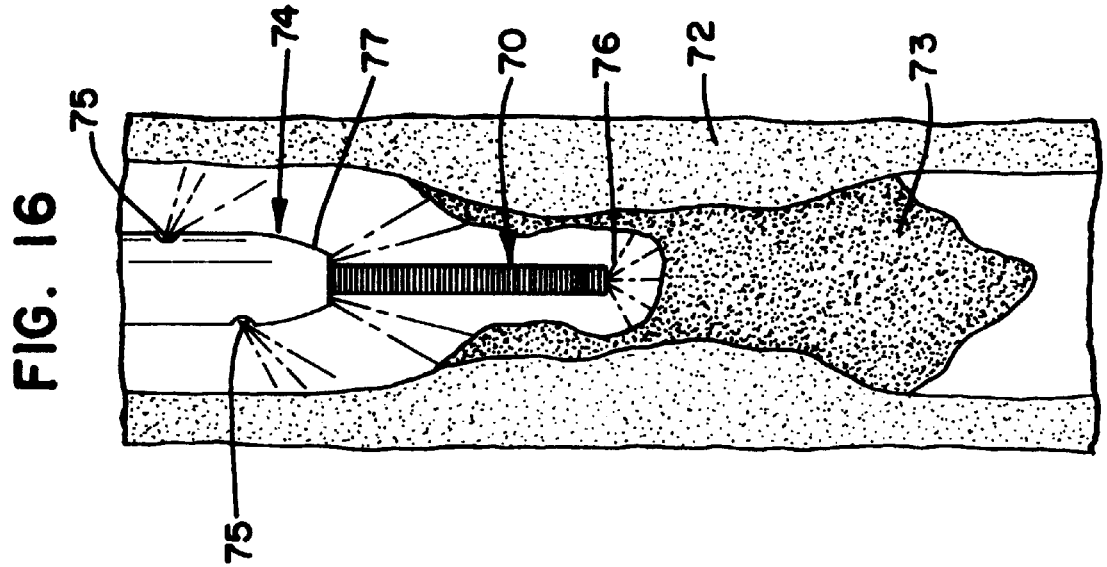
FIG. 16 is an elevational view of a representative combination catheter type and end hole guidewire type drug infusion catheter/guidewire device with portions broken away after it has been advanced into a blood vessel of a patient and the core wire has been withdrawn.

In use, the flexible tubular member and removable core would be advanced together through the patient's circulatory system like a conventional guidewire until reaching the desired location. Therefore, the use of a flexible tubular member 20 in accordance with the various embodiments of the invention previously described in the discussion on guidewires provides the guidewire type drug infusion catheter/guidewire with the required flexibility and torquability to maneuver the device through the circulatory system. After reaching the desired location, the core is removed leaving only the flexible tubular member 20 within the patient. Drugs or other fluids can then be pumped through the lumen of the flexible tubular member 20 and out the holes 71 and into the occluded portion of the blood vessel 72. As shown in FIG. 16, a second embodiment of a guidewire type drug infusion catheter/guidewire 70 could be made very similar to the previously described device in FIG. 15 except that the second embodiment would contain a hole in the distal end 76 and would not contain side holes 71 as shown in FIG. 15.

However, because the outside diameters of the flexible tubular member 20 in the guidewire type drug infusion catheter/guidewire devices are sized like guidewires, the lumen size of the flexible tubular member is limited. Therefore, the flowrate of drugs through the lumen is limited. If a larger flowrate or if a similar flowrate must be supplied with a lower source pressure, a catheter type drug infusion catheter/guidewire 74 might be used. The catheter type drug infusion catheter/guidewire 74 would be comprised of a flexible tubular member 20 made in accordance with the previously described embodiments of the invention for use as a catheter, except that it would have a tapered distal end 77 and side holes 75 near its distal end 77. The catheter type drug infusion catheter/guidewire 74 would be advanced over a guidewire or a guidewire type drug infusion catheter/guidewire 70, as shown in FIG. 16. Upon reaching the desired location, drugs or other fluids would be pumped through the catheter type drug infusion catheter/guidewire 74 and through the side holes 75 into the blood vessel near the occluded location. Because the catheter type drug infusion devices 74 have a larger lumen than the guidewire type drug infusion devices 70, the drugs or other fluids can be delivered to the desired area at a lower pressure.

It is to be understood, however, that even though numerous characteristics and advantages of the present invention have been set forth above in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A method for producing a flexible tubular medical device comprising:
   providing a tubular element sized for vascular insertion in a human body, the tubular element including an outer surface;
   providing a light source;
   applying a photoresist to at least a portion of the outer surface of the tubular element;
   providing a pattern mask intermediate the tubular element and the light source;
   exposing the photoresist by directing light from the light source through the pattern mask, and generating relative movement between the tubular element and the light source such that an exposed pattern and an unexposed pattern are generated on the outer surface of the tubular element;
   developing the photoresist to remove first regions of the photoresist that correspond to one of the exposed and unexposed patterns; and
   removing first portions of the tubular element that correspond to the first regions of the photoresist such that the tubular element is provided with a desired pattern, the desired pattern including a plurality of apertures that extend completely through the tubular element between an inner and outer diameter of the tubular element, the plurality of apertures being arranged and configured for providing the tubular element with a desired flexibility suitable for intravascular operations.

2. The method of claim 1, wherein the pattern mask is on a tube.

3. The method of claim 1, wherein the pattern mask is on a film.

4. The method of claim 3, wherein said film is curved.

5. The method of claim 1, wherein said pattern mask is a curved film or a tube including at least two regions having differently configured patterns.

6. The method of claim 1, wherein the photoresist on the tubular element is either a positive photoresist or a negative photoresist.

7. The method of claim 1, wherein the first portions of the tubular element are removed by chemical etching.

8. The method of claim 1, additionally comprising removing any remaining photoresist.

9. The method of claim 1, wherein the flexible tubular device is a catheter.

10. The method of claim 1, wherein the flexible tubular device is a catheter sheath.

11. The method of claim 1, wherein the flexible tubular device is a drug infusion catheter.

12. The method of claim 1, wherein the light source is selectively activated and de-activated in coordination with the relative movement between the tubular element and the light source.

13. A method for producing a flexible tubular medical device comprising:
   a. providing a tubular element sized for vascular insertion in a human body, the tubular element including an outer surface;
   b. providing a light source;
   c. creating a pattern on the tubular element by:
      1. applying photoresist to at least a portion of the outer surface of the tubular element;
      2. providing a mask intermediate the tubular element and the light source, said mask being curved, at least a portion of said curvature including a pattern defining a plurality of locations translucent to light from the light source;
      3. placing said tubular element into contact with said mask such that a curvature of said mask receives said tubular element along a first partial arc;
      4. activating said light source to expose areas of the photoresist on the tubular element that are located along said first partial arc;
      5. developing the photoresist on the tubular element such that first portions of the photoresist are removed from the tubular element while second portions of the photoresist remain on the tubular element, the first portions and the second portions corresponding to their respective exposure from the light source; and
   d. removing segments of the tubular element corresponding to the first portions of the photoresist such that the tubular element is provided with a desired pattern, the desired pattern including a plurality of apertures that extend completely through the tubular element between an inner and outer diameter of the tubular element, the plurality of apertures being arranged and configured for providing the tubular element with a desired flexibility suitable for intravascular operations.

14. The method of claim 13, wherein step (c) further comprises:

prior to development, moving the tubular element such that at least a second partial arc of the tubular element is in contact with said predetermined locations translucent to light from the light source; and activating said light source to expose said second partial arc of said tubular element.

15. A method for producing a flexible tubular medical device comprising:

a. providing a tubular element sized for vascular insertion in a human body, the tubular element including an outer surface;

b. providing a light source;

c. creating a pattern on the tubular element by:
1. applying a photoresist to at least a portion of the outer surface of the tubular element;
2. providing a mask intermediate the tubular element and the light source, at least a portion of the mask including a predetermined pattern formed of predetermined locations translucent to light from the light source;
3. placing a portion of said mask, said portion including a pattern having a plurality of locations translucent to light from the light source, into contact with said tubular element along a partial arc of said tubular element;
4. activating said light source to expose areas of the photoresist along said partial arc of said tubular element;
5. developing the photoresist on the tubular element such that first portions of the photoresist are removed from the tubular element while second portions of the photoresist remain on the tubular element, the first portions and the second portions corresponding to their respective exposure from the light source; and d. removing segments of the tubular element corresponding to the first portions of the photoresist such that the tubular element is provided with a desired pattern, the desired pattern including a plurality of apertures that extend completely through the tubular element between an inner and outer diameter of the tubular element, the plurality of apertures being arranged and configured for providing the tubular element with a desired flexibility suitable for intravascular operations.

16. The method of claim 15, wherein said partial arc is a first partial arc; and step (c)(4) further comprises:

moving the tubular element such that at least a second partial arc length of the tubular element is in contact with said predetermined locations translucent to light from the light source on said mask; and activating said light source to expose said second partial arc length of said tubular element.

17. The method of claim 16, wherein the mask includes a film and step (c)(3) further comprises:

rotating the tubular element while moving the film relative to both the tubular element and the light source, said film continuously contacting said tubular element along said partial arc.

18. A method for producing a flexible tubular medical device comprising:

providing a tubular element sized for vascular insertion in a human body, the tubular element including an outer surface;

providing a light source;

applying a photoresist to at least a portion of the outer surface of the tubular element;

providing a glass pattern mask intermediate the tubular element and the light source;

exposing the photoresist by directing light from the light source through the pattern mask such that an exposed pattern and an unexposed pattern are generated on the outer surface of the tubular element;

developing the photoresist to remove first regions of the photoresist that correspond to one of the exposed and unexposed patterns; and removing first portions of the tubular element that correspond to the first regions of the photoresist such that the tubular element is provided with a desired pattern, the desired pattern including a plurality of apertures that extend completely through the tubular element between an inner and outer diameter of the tubular element, the plurality of apertures being arranged and configured for providing the tubular element with a desired flexibility suitable for intravascular operations.

19. The method of claim 18, wherein during the exposing step, relative movement is generated between the light source and the tubular element, and relative motion is generated between the pattern mask and both the light source and the tubular element.

20. The method of claim 18, wherein the pattern mask comprises a patterned glass tube that is concentrically positioned about the tubular element.

21. The method of claim 18, wherein during the exposing step, the light source remains stationary, the tubular element is rotated in a first direction, and the pattern mask is moved across the tubular element in coordination with the rotation of the tubular element.

22. The method of claim 18, wherein the pattern mask is curved.

23. A method for producing a flexible tubular medical device comprising:

providing a tubular element sized for vascular insertion in a human body, the tubular element including an outer surface;

providing a light source;

applying a photoresist to at least a portion of the outer surface of the tubular element;

providing a pattern mask intermediate the tubular element and the light source;

exposing the photoresist by directing light from the light source through the pattern mask such that an exposed pattern and an unexposed pattern are generated on the outer surface of the tubular element, wherein the exposed and unexposed patterns are generated by rotating the tubular element relative to the light, and moving the pattern mask across the tubular element in coordination with the rotation of the tubular element;

developing the photoresist to remove first regions of the photoresist that correspond to one of the exposed and unexposed patterns; and removing first portions of the tubular element that correspond to the first regions of the photoresist such that the tubular element is provided with, a desired pattern, the desired pattern including a plurality of apertures that extend completely through the tubular element between an inner and outer diameter of the tubular element, the plurality of apertures being arranged and configured for providing the tubular element with a desired flexibility suitable for intravascular operations.

24. The method of claim 23, wherein the pattern mask is moved along a curved path.

25. The method of claim 23, wherein the pattern mask is moved along a generally linear path.

26. A method for producing a tubular medical device comprising:

provided a tubular element including a circumferential outer surface defined by at least first and second separate partial arc surfaces;

providing a light source;

applying a photoresist to the first and second partial arc surfaces of the tubular element;

providing a pattern mask intermediate the tubular element and the light source, generating an exposure pattern on the photoresist by:
facing the first partial arc surface toward the light source;

exposing the photoresist on the first partial arc surface by directing light from the light source through the pattern mask and onto the photoresist that covers the first partial arc surface;

rotating the tubular element such that the second partial arc surface faces the light source;

moving the pattern mask relative to the tubular element; and exposing the photoresist on the second partial arc surface by directing light from the light source through the pattern mask and onto the photoresist that covers the second partial arc surface;

developing the photoresist; and removing portions of the tubular element that correspond to the exposure pattern generated on the outer surface of the tubular element.

27. The method of claim 26, wherein the pattern mask is moved along a curved path.

28. The method of claim 26, wherein the pattern mask is moved along a generally linear path.

29. The method of claim 26, wherein the pattern mask contacts the tubular element.

* * * * *